(12) United States Patent
Roach et al.

(10) Patent No.: US 8,940,232 B2
(45) Date of Patent: *Jan. 27, 2015

(54) AUTOMATED MICRO-VOLUME ASSAY SYSTEM

(71) Applicant: ProteinSimple, Santa Clara, CA (US)

(72) Inventors: David J. Roach, Los Gatos, CA (US); Tom W. Yang, Cupertino, CA (US); Roger A. O'Neill, San Carlos, CA (US); Robert T. Loder, Jr., Sunnyvale, CA (US)

(73) Assignee: ProteinSimple, Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/778,757

(22) Filed: Feb. 27, 2013

(65) Prior Publication Data

US 2013/0167937 A1   Jul. 4, 2013

Related U.S. Application Data

(60) Division of application No. 13/236,316, filed on Sep. 19, 2011, now abandoned, which is a continuation of application No. 11/401,699, filed on Apr. 10, 2006, now Pat. No. 8,021,611.

(60) Provisional application No. 60/669,694, filed on Apr. 9, 2005.

(51) Int. Cl.
| | |
|---|---|
| *B01L 9/00* | (2006.01) |
| *B01L 3/02* | (2006.01) |
| *G01N 1/14* | (2006.01) |
| *G01N 35/10* | (2006.01) |
| *F16L 41/00* | (2006.01) |
| *G01N 35/04* | (2006.01) |

(52) U.S. Cl.
CPC ............... *F16L 41/00* (2013.01); *G01N 35/04* (2013.01); *G01N 35/1065* (2013.01); *G01N 2035/1034* (2013.01); *G01N 2035/1039* (2013.01); *G01N 2035/1051* (2013.01); *G01N 2035/1062* (2013.01)
USPC ............ 422/63; 422/562; 422/501; 422/509; 422/518; 422/520; 422/68.1; 436/180; 436/43; 436/54

(58) Field of Classification Search
CPC ............. G01N 35/10; G01N 35/1011; G01N 35/0099; A47L 9/02
USPC ............................ 422/500–570; 436/180, 43
See application file for complete search history.

(56) References Cited

U.S. PATENT DOCUMENTS

| | | | | |
|---|---|---|---|---|
| 3,915,652 A | * | 10/1975 | Natelson | 422/65 |
| 4,960,566 A | * | 10/1990 | Mochida | 422/65 |
| 5,479,969 A | * | 1/1996 | Hardie et al. | 141/130 |
| 5,798,035 A | * | 8/1998 | Kirk et al. | 506/4 |

(Continued)

*Primary Examiner* — Brian R Gordon

(57) ABSTRACT

An automated assay system is described with stations for placement of materials to be used in an assay of materials inside capillaries and an automated gripper for manipulating capillaries. The system includes a separation and immobilization station where reactions inside the capillaries take place and a detector station where photoemissions from the capillary reactions are detected. The photoemissions from the capillaries may be displayed as line graphs or in columns of a pseudo-gel image resembling the familiar Western gel blot. An automated control system has a user interface by which an operator can select a run protocol and define the locations of samples and reagents to be used in the protocol run: Following the setup the control system will cause the automated system to execute the protocol, then display the results in a selected display format.

13 Claims, 24 Drawing Sheets

(56) References Cited

U.S. PATENT DOCUMENTS

| | | | |
|---|---|---|---|
| 5,976,896 A * | 11/1999 | Kumar et al. | 436/527 |
| 6,423,536 B1 * | 7/2002 | Jovanovich et al. | 435/287.2 |
| 7,235,215 B2 * | 6/2007 | Velghe et al. | 422/520 |
| 7,300,523 B2 * | 11/2007 | Lee et al. | 134/18 |
| 2002/0110900 A1 * | 8/2002 | Jovanovich et al. | 435/286.4 |
| 2003/0180189 A1 * | 9/2003 | Velghe et al. | 422/100 |
| 2004/0062686 A1 * | 4/2004 | Ganz et al. | 422/100 |
| 2004/0072365 A1 * | 4/2004 | Rose et al. | 436/180 |

* cited by examiner

Reagent Registration

Ampholyte
- Ampholyte ID *
- Lowest pH value *
- Highest pH value * pI Standard
- pI Standard ID *
- Number of standards *
- List of pH values for each standard *

Antibody
- Antibody ID *
- Primary * | anti-AKT
- Secondary * | Anti-mouse
- Antigen
- Synonym
- Host
- Supplier
- Catalog/Product Number
- Accession number for protein (antigen)
- For primary antibodies:
  expected pH of antigen-antibody complex

* – Required Information

FIG. 12

Sample Tracking

Protein/Lysate Sample
- Well Location *
- Sample Name *
- Treatment Dose
- Time Course Interval
- Cell Line or Type
- Concentration
- Name or ID of pI standards solution *
- Name or ID of ampholyte solution *

Antibody
  Primary                                     Secondary
    o Well Location  * B: Row C         Well Location  * B: Row E
    o Antibody ID    * anti-AKT         Antibody ID    * Anti-mouse
    o Concentration                    Concentration Blocking/Wash Solution
- Well Location *
- Solution Name *
- Concentration \* — Required Information

FIG. 14

| | 1 | 2 | 3 | 4 | 5 | 6 | 7 | 8 | 9 | 10 | 11 | 12 |
|---|---|---|---|---|---|---|---|---|---|---|---|---|
| Sample Name | akt 100ng/mL | akt 90ng/mL | akt 80ng/mL | akt 70ng/mL | akt 60ng/mL | akt 50ng/mL | akt 40ng/mL | akt 30ng/mL | akt 20ng/mL | akt 10ng/mL | akt 5ng/mL | akt 2ng/mL |
| Primary Antibody | anti-AKT | anti-AKT | anti-AKT | anti-AKT | anti-AKT | anti-AKT | anti-AKT | anti-AKT | anti-AKT | anti-AKT | anti-AKT | anti-AKT |
| Secondary Antibody | Anti-mouse | Anti-mouse | Anti-mouse | Anti-mouse | Anti-mouse | Anti-mouse | Anti-mouse | Anti-mouse | Anti-mouse | Anti-mouse | Anti-mouse | Anti-mouse |
| Blocking Solution | CB2533 | CB2533 | CB2533 | CB2533 | CB2533 | CB2533 | CB2533 | CB2533 | CB2533 | CB2533 | CB2533 | CB2533 |

FIG. 15

AUTOMATED MICRO-VOLUME ASSAY SYSTEM

CROSS REFERENCE TO RELATED APPLICATIONS

This application is a divisional of U.S. patent application Ser. No. 13/236,316, filed Sep. 19, 2011, entitled "Automated Micro-Volume Assay System," which is a continuation of U.S. patent application Ser. No. 11/401,699, filed Apr. 10, 2006, and entitled "Automated Micro-Volume Assay System," now U.S. Pat. No. 8,021,611, which claims the benefit of, and priority to, U.S. Provisional Patent Application Ser. No. 60/669,694 filed on Apr. 9, 2005, and entitled "Automated Micro-Volume Assay System," each of which is incorporated herein by reference in its entirety.

FIELD OF THE INVENTION

This invention generally relates to an assay system for assaying volumes of biological substances of microliter sizes and smaller and, in particular, to a micro-volume assay system which is automated.

BACKGROUND

A number of methods and systems have been developed for conducting various processing and/or analyses of biological substances, such as those described in U.S. Pat. No. 6,423,536 for temperature cycling processes, U.S. Pat. Nos. 5,843.680, 5,784,154, 5,395,502, and 5,137,609 for separation assay methods, U.S. Pat. No. 5,785,926 for a capillary transport system, international publication WO94/13829 for an isoelectric focusing separation assay system, and U.S. Pat. No. 6,430,512 for a chromatographic fluorescence separation and display system.

U.S. patent application Ser. No. 60/589,139, filed Jul. 19, 2004 and entitled "CONTINUOUS DETERMINATION OF CELLULAR CONTENTS BY CHEMILUMINESCENCE", U.S. patent application Ser. No. 60/617,362, filed Oct. 8, 2004 and entitled "DETERMINATION OF CAPTURED CELLULAR CONTENTS", and U.S. patent application Ser. No. 11/185,247, filed Jul. 19, 2005 and entitled "METHODS AND DEVICES FOR ANALYTE DETECTION", and U.S. patent application Ser. No. 10/139,100 entitled MICROFLUIDIC DEVICE FOR ANALYZING NUCLEIC ACIDS AND/OR PROTEINS, METHODS OF PREPARATION AND USES THEREOF, the disclosures of all of which are incorporated herein by reference, all describe apparatus and methods for assaying microliter volumes of cellular material by separating constituent substances of the material in a fluid chamber such as a capillary, binding the separated substances in place, then eliciting an optical response from the bound substances such as fluorescence or chemiluminescence. The resulting information has content similar to that of a Western gel blot but without the complex, extensive and time-consuming handling and processing steps that adversely affect reproducibility and make automation difficult. This technique also has advantages such as the ability to assay very small volumes of materials such as those on the cellular level, and good sensitivity due to the ability to receive optical data from chemiluminescence for as long as necessary to obtain a desirable output signal level. However, it would be desirable to automate this technique so that multiple samples may be analyzed simultaneously or in rapid succession with ease and robustness while only consuming minimal volumes of precious reagents and expensive disposables. Thus, further developments are needed.

SUMMARY

In accordance with the principles of the present invention an assay system is presented. In some embodiments, the system of the present invention is configured to provide the functionality of both pipettes and fluid paths for analysis in a single system. For example, in some embodiments the system of the present invention uses capillaries, or other devices having a small internal dimension such as microchannels, as both pipettes and as the fluid paths for analysis. This enables analysis of very small volume samples, and among other advantages significantly improves overall fluid consumption as well as simplifying automation and improving robustness. In some embodiments the system provides sampling and analyzing small volume samples of biological material and conducting one or more of electrophoretic or isoelectric focusing separation, immobilization, and fluorescent and chemiluminescent detection under automated control. Multiple capillaries can be processed in parallel through the system or, to conserve reagents and/or a precious sample, multiple capillaries can be moved in parallel but filled sequentially from a single well for each different fluid under automated control. In some embodiments a manifold is provided which enables flowing fluid through multiple capillaries simultaneously by vacuum, pressure or electrophoretic action. The detection data produced can be received from multiple spatial locations at the same time and comparatively presented in the standard "ladder" display of a Western gel blot.

In one aspect, embodiments of the present invention provides automated assay systems comprising: a processing station; and an automated capillary gripper which is operable to load one or more capillaries with one or more reagents or samples and position the loaded capillaries at the processing station. In another embodiment a detection station is also provided and the automated capillary gripper is operable to position the one or more capillaries containing the reagents or samples at a selected one of the processing station or the detection station.

In other aspects a capillary holder is provided comprising: first and second fluid reservoirs; a plurality of recesses which retain a plurality of capillaries in position in the holder with the ends of the capillaries located at the first and second reservoirs; and electrodes in contact with each of the first and second fluid reservoirs, wherein fluids in the reservoirs are retained at the respective ends of the capillaries by surface tension.

In yet another aspect, an apparatus operable to fill one or more capillaries with fluid is provided, comprising: a device configured to support one or more capillaries and a manifold containing a source of vacuum and having a plurality of apertures which engage the ends of one or more capillaries while fluid is drawn into the capillaries.

Further, in some embodiments methods of conducting an experiment are provided, comprising the steps of: gripping one or more capillaries with an automated capillary gripper; loading one or more samples into the one or more capillaries by maneuvering an end of the capillary into contact with a sample by operation of the automated capillary gripper; and placing the loaded capillary in a processing station.

In another aspect, embodiments of the invention provide an operating system for an automated assay system. The assay system includes an automated capillary gripper responsive to the operating system which manipulates capillaries, and a processing station. The operating system comprises operator input means for selecting a protocol; operator input means for identifying the location of a capillary; and operator input means for identifying the location of a sample/reagent, wherein the automated capillary gripper operates in response to the information input by the operator input means. In some embodiments the sample/reagent station further comprises a first sample station and a second reagent station, wherein the operator input means for identifying the location of a sample/reagent comprises. An operator input means for identifying the location of a sample at the sample station to be used during execution of the protocol is also provided, and an operator input means for identifying the location of a reagent at the reagent station to be used during execution of the protocol.

Embodiments of the invention further provide methods of operating an automated assay system, where the assay system includes a computer program responsive to emissions from one or more capillaries which produces a display of analytical results. In some embodiments the method comprises producing a display of adjacent bands depicting the one or more capillary emissions. In some embodiments emissions comprise photoemissions from materials inside the capillaries, and the step of selecting further comprises identifying the materials inside respective ones of the capillaries. Additionally, the step of producing may further comprises concurrently producing a display of source locations of materials inside the capillaries; and the step of selecting further comprises identifying the sources of the materials inside respective ones of the capillaries by means of the source location display. In some embodiments, the source location display comprises a display of a microtiter plate images including microwells wherein the display of adjacent bands comprises a pseudo-gel display; and the step of selecting further comprises selecting microwells of the microtiter plate image to select capillary photoemissions for display in respective bands of the pseudo-gel display.

Another aspect of the present invention a kit is provide comprising the assay system described herein and any one or more of: a plurality of capillaries, one or more reagents, or one or more samples.

Additional embodiments provide methods of conducting an experiment with an automated assay system having stations at which one or more of assay samples, capillaries, and reagents may be located and an automated mechanism for manipulating these materials, comprising the steps of: inputting setup information defining the materials to be used in the experiment; inputting setup information defining the locations of the materials at the stations; defining a run to be conducted using the defined materials; simulating the run for the defined materials at the defined locations; and conducting the run using the defined materials at the defined locations.

BRIEF DESCRIPTION OF THE FIGURES

Other objects and advantages of the invention become apparent upon reading of the detailed description of the invention and the appended claims provided below, and upon reference to the drawings, in which:

FIG. 12 is a screen shot of a graphical user interface showing a reagent listing.

FIG. 14 is a screen shot of a graphical user interface showing the locations and identities of samples, antibodies, and fluids for a run in accordance with embodiments of the present invention.

FIG. 15 illustrates a screen shot of a graphical user interface listing the samples and reagents for capillaries of a capillary holder in tabular form.

DETAILED DESCRIPTION

In accordance with the principles of the present invention an assay system is presented. In some embodiments, the system of the present invention is configured to provide the functionality of both pipettes and fluid paths for analysis in a single system. This enables analysis of very small volume samples, and among other advantages improves overall fluid consumption as well as simplifying automation and improving robustness.

Figure 1:
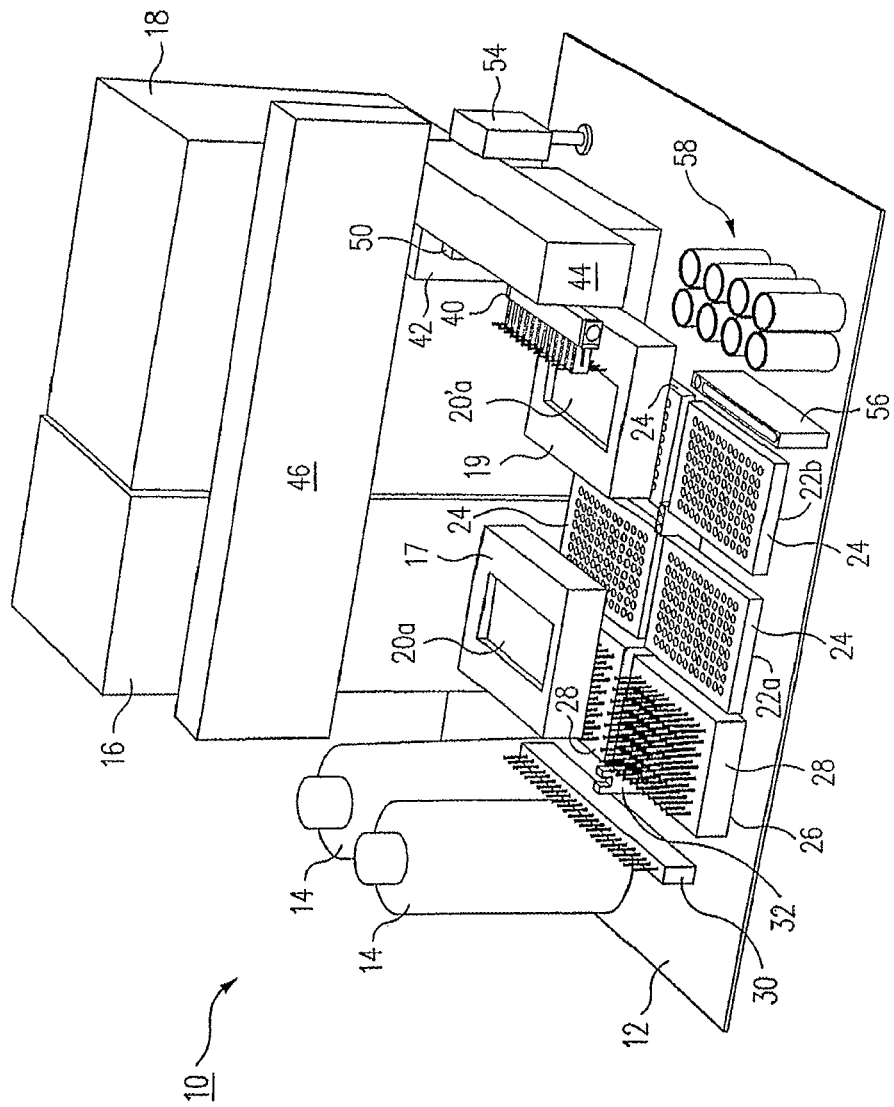
FIGS. 1 and 2 are front perspective views of an immunoassay system constructed in accordance with principles of the present invention.
Figure 2:
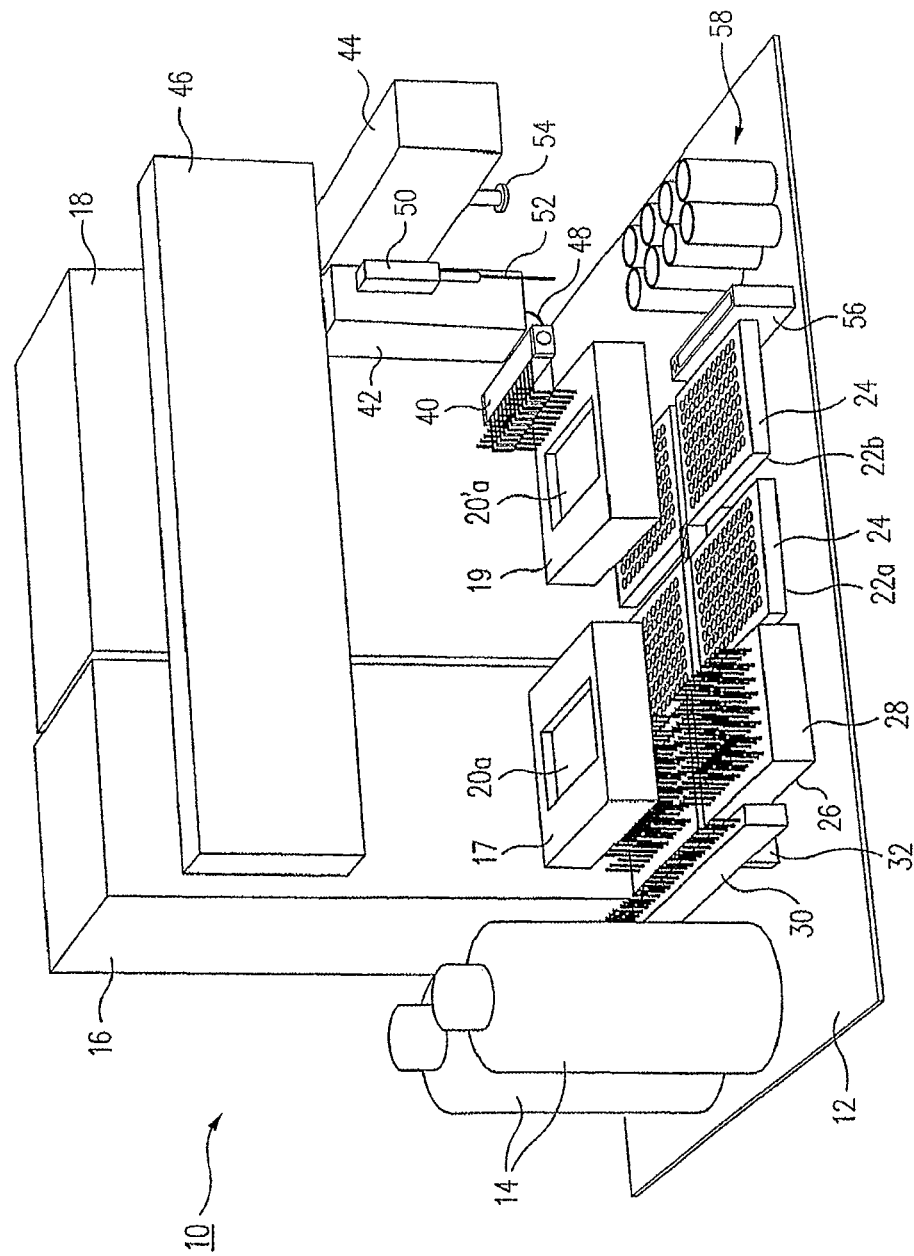

Referring first to FIGS. 1 and 2 a immunoassay system 10 constructed in accordance with principles of the present invention is shown in a perspective view. In the illustrative embodiment, the system 10 is mounted on a baseplate 12 with a surface suitable for wipe down if biohazardous materials are processed though the system (e.g., stainless steel or plastic). Shown on the baseplate 12 are a pair of bottles 14 which contain bulk fluids. Clean wash fluid is pumped for use from one bottle while all system waste fluids are pumped into the other bottle. Toward the back of the baseplate 12 is a detection module 16. The detection module 16 houses a movable tray 17 with a space 20$a$ for a capillary holder 20'(shown in FIG. 3$a$) and an intermediate holder 20" (shown in FIG. 3$e$). The movable tray 17 is automated to slide into and out from the detection module in the manner of a disk tray of a computer optical disk drive to transport the capillary holders into and out of the module 16. The detection module houses an imaging optical detector for detecting light emitted from within the capillaries. In this embodiment the optical detector is a cooled charge-coupled device (CCD) array detector. Light from the capillaries is imaged onto the CCD by a lens assembly. The detection module is light-tight when the tray 17 is retracted to the interior of the module, enabling the CCD array detector to detect light emitted from a capillary by chemiluminescence or fluorescence. To excite fluorescence an array of light emitting diodes inside the detection module is arranged to uniformly illuminate the capillaries. Alternatively, a laser or other light source could be used for excitation. Wavelength-selective filters are used to prevent excitation light, emitted from the light emitting diodes, from interfering with detection of the fluorescent emissions. For chemiluminescent detection a material such as luminol is flowed through the capillaries by hydrodynamic flow as described below and the emitted photons are detected by the CCD array detector. In an alternative embodiment luminol may be electrically pumped through the capillaries by application of voltage across the capillaries with hardware similar to that described in the section below for isoelectric focusing. During detection the capillary is held in a capillary holder 20' on the tray 17 which is retracted into the detection module and moves out again after photodetection is completed. The detection process may take from seconds to hours depending on the level of sensitivity desired.

As referred to herein, the term capillary or capillaries is meant to include any device that has one or more internal tubes or bore with a small dimension. The internal tube(s) can have any suitable shape, and for example may be circular, square, triangular, and the like. The term capillary or capillaries include multiple internal tubes, and for example include microfabricated devices that contain internal channels as the tubes. Generally, the internal tube(s) have any suitable dimension. In some embodiments the dimension of the internal tube(s) is in the range of 1 micron to 2000 microns. In other embodiments, the dimension of the internal tube(s) is in the range of 25 microns to 250 microns. In some embodiment, the length of the internal tube(s) is in the range of 30 mm to 100 mm. The external size and shape of the capillaries are not limited.

The capillary holder is described in greater detail in FIGS. 3$a$-3$e$. The capillary holder may hold a plurality of capillaries so that the CCD array will detect photoemissions from a plurality of capillaries at the same time. In an alternate embodiment a scanning fluorescence detector may be used. In that embodiment excitation light focused by a lens irradiates fluorescent molecules within each capillary. This same (or another) lens collects the resulting fluorescent emission for detection by a photo sensitive device such as a photo-multiplier tube. This focused excitation/collection can be scanned along the length of each capillary individually or in groups. The excitation light is a coherent source such as a laser or an incoherent source such as an arc lamp or light emitting diode array.

Adjacent to the detection module 16 is a processing station 18. In one embodiment the processing station 18 performs either separation and/or capture. In another embodiment, the processing station 18 can perform separation, capture and detection. Referring to the exemplary embodiment illustrated in the figures where both separation and capture are preformed, processing station 18 includes separation and immobilization module. In some embodiments this module comprises a movable tray 19 with a space 20'$a$ for a capillary holder 20' and intermediate holder 20" and the electronics for conducting electrophoresis and isoelectric focusing of substances in the capillaries when the capillaries are located in a capillary holder 20'. As described below in an illustrative embodiment, the capillary holder 20' has two integrated electrodes that are electrically connected to respective fluid reservoirs on opposite sides of the capillary holder. The ends of the capillaries (see FIG. 3$c$) in the capillary holder are in fluidic contact with the fluids in these two reservoirs. Thus, when the separation and immobilization module 18 applies a voltage across the electrodes, this voltage is applied across the fluid paths within the capillaries in the capillary holder 20'. The voltage applied to the capillaries is regulated by a computer controlled power supply (not shown) located inside or coupled to the module 18. This voltage causes the biological molecules to separate by isoelectric focusing. In an alternate embodiment, the molecules may be separated by size or other techniques.

Following separation of the biological molecules in the fluid paths of the capillaries in accordance with their ionic charge by isoelectric focusing, the separated molecules are immobilized in their focused positions in the capillaries. In the illustrated embodiment this is accomplished by irradiating the capillaries with ultraviolet light from a UV light source inside the separation and immobilization module to bind the separated material to either a material within the lumen or to the walls of the capillaries by photoactivated chemistry. Typically UV light is used at an intensity in the range of 1-1000 mW/cm2 for a period of time in the range of 1-200 s. The isoelectrically focused materials are thereafter detected in the detection module 16. It may be desirable in some situations to retain the capillary holder 20' in a level position to minimize hydrodynamic flow through the capillaries during focusing and immobilization. Alternatively, increasing fluid viscosity will reduce fluid flow. Yet another approach is to incorporate a small connecting fluid path (e.g., a channel) between the two reservoirs of the capillary holder. This path would typically be about 1 mm across, so that the fluid heights between the two reservoirs will quickly equalize.

Located on the baseplate 12 in this embodiment are a number of microwell plate stations 22$a$-22$d$. In the illustrations of FIGS. 1 and 2 there is shown a microwell plate 24 located in each of the stations 22$a$-22$d$. Preferably the microwell plate(s) containing samples are chilled while in these stations. This may be accomplished preferably by thermoelectric cooling or by other means such as refrigeration, recirculating cold fluid or an ice bath coupled to the sample plates. The stations have guides or recesses which precisely define the locations of standard microwell plates when located in the stations. Each microwell plate station in this embodiment is marked on the baseplate 12 by a distinguishing color or graphic which is visible through a translucent microwell plate, enabling each station to be distinctively identified as discussed below. A standard microwell plate may contain 96 microwells on a 9 mm center-to-center spacing or 384 microwells on a 4.5 mm center-to-center spacing. Plates with other spacings and numbers of wells may be used and the invention is not intended to be limited to any one specific configuration.

In some embodiments, a robotic, computer-controlled capillary manipulator as described herein accesses a preselected well in a microwell plate 24, the plates and each of their wells being in specific, predefined positions on stations 22a-22d. Computer control enables the specification of the microwell plate to be chosen from several predetermined standards to which the capillary manipulator is programmed. Also located on the baseplate 12 in this embodiment are a pair of bulk capillary rack stations 26. As in the case of the microwell plate stations, the capillary rack stations locate standardized capillary racks 28 in predetermined locations so that capillaries in the racks 28 can be automatically accessed by a robotic computer-controlled capillary manipulator to pick up capillaries from the racks 28. A capillary rack 28 may contain 96 capillaries on a 9 mm center-to-center spacing or 384 capillaries on a 4.5 mm center-to-center spacing. If the capillaries utilize an internal wall coating for immobilization, they may be supplied precoated in the racks.

Capillaries are preferably made from a transparent low fluorescence material such as glass that is also rigid and straight. Various inside diameters (typically 10 μm to 1 mm) and lengths (typically 30 mm to 100 mm) are commonly used. In one embodiment, a capillary is 40 mm in length with an internal diameter of 100 μm, giving the capillary a volume of 314 microliters. Various cross sectional shapes, both inside and outside, are also possible. One could also use different materials such as plastic. The invention is not limited by the type or configuration of any one type of capillary and any suitable capillary may be employed.

In an alternative embodiment a microfabricated device may be used in place of individual capillaries or a combination thereof. In some embodiments microfabricated devices are fabricated with internal capillary channels whose dimensions would be similar to those described previously for capillaries. A microfabricated device can be fabricated from various materials such as silicon, glass or plastic and may contain integrated electrodes, electronics and valves. They may be disposable or re-usable devices. Microfabricated devices can contain from one to hundreds of channels that can be controllable individually or in parallel or some combination thereof. A typical microfabricated device contains wells for adding samples or other reagents. External electrodes may also be inserted into these wells. As with capillaries, the cross section of a capillary channel is not constrained to any particular shape.

In the illustrated embodiment capillaries are removed from a storage rack 28 of, for example, ninety-six capillaries, by a robotic, computer-controlled capillary manipulator and placed prior to use into a capillary staging rack 30. In this embodiment the staging rack 30 has locations for 24 individual capillaries in a single row. The staging rack positions the lower end of each capillary at a specified height. This insures that each capillary processed through the system will make contact with fluid in a microwell plate filled to a specific level. The staging rack also allows the capillary manipulator, under computer control, to withdraw from 1 to 12 capillaries for processing. When at least 12 capillaries have been withdrawn from the rack, the capillary manipulator then transfers a row of 12 capillaries from the capillary rack 28 and places them immediately adjacent to any remaining capillaries in staging rack 30. The staging rack is movable between two positions fore and aft under computer control so that capillaries are always withdrawn contiguously from one end of staging rack 30. This insures that when 12 or fewer capillaries remain in the staging rack there will be at least 12 contiguous positions into which a row of 12 capillaries can be transferred from capillary rack 28.

Adjacent to the staging rack 30 is an optical capillary detector 32. The optical detector contains a light source and a photocell on opposite sides of a slot in the top of the detector 32. For sufficiently large capillaries, this device may be what is commonly described in the field of electronics as a photo-interrupter. Whenever it is desirable to verify that a capillary is being held in a particular position by a capillary manipulator, the capillary manipulator is moved to pass the capillary through the slot of the detector 32. If there is a capillary in the particular position of the manipulator it will interrupt the light beam between the source and the photocell. This interruption is sensed by the computer controlling the capillary manipulator which then is assured that a capillary is in the tested position of the capillary manipulator.

In accordance with principles of the present invention the immunoassay system 10 includes a capillary manipulator comprising a capillary gripper 40 mounted on robotic actuators 42, 44 and 46. In one embodiment the robotic actuators 42, 44, 46 are motorized linear translation stages and are arranged to provide x, y, z motion control although other actuator mechanisms could also be employed as long as they are computer controllable. The gripper 40 can move up and down by operation of the up-down actuator 42. The actuator 42 is moved from front to back by actuator 44. Actuator 44 in turn is moved between the left and right sides of the system 10 by and in relation to actuator 46. In FIGS. 1 and 2 the gripper 40 is seen to be holding twelve capillaries in a vertical orientation in which the capillaries are generally transported and filled. However, the gripper is hinged at its connection to the actuator 42 by a hinge 48 so that it can be controllably pivoted 90°, thereby moving the capillaries to a horizontal orientation. When the gripper and capillaries are in this orientation, capillaries can be put into and removed from the capillary holders 20' and 20''. The combined actuator mechanisms thus can traverse all of the elements of the system in front of the detection and separation and immobilization modules.

In the illustrative embodiment, the robotic actuators 42, 44, 46 manipulate four tools. In addition to the gripper 40 the robotic actuators manipulate a lid remover 54, a pipette 52 connected to a syringe pump 50 and a reformatting gripper 40a, shown in FIG. 9. When one of the three tools 54, 52, 40a is to be used, it is lowered to a position below the level of gripper 40 by a respective vertical actuator (not shown) and then into an operating position by actuators 42, 44, 46. This prevents one tool from interfering with any other tool during use. The lid remover performs tasks such as removing lids which cover the microwell plates to prevent evaporation of the fluids inside the microwells. The lid remover does this by first lowering into position over the lid to be removed, applying suction created by a vacuum source to hold the lid and then raising up to lift the lid off the microwell plate. The lids (if used) of the small bottles 58 can also be removed and replaced by the lid remover 54 in a similar manner. In an alternative embodiment, the wells of the microwell plates 24 may be foil sealed prior to being placed into the system 10. When fluid access is required, the seal could be punctured with a tool carried by actuators 42, 44, 46 to expose the well(s) to be accessed. The pipette 52 performs precise fluid transport such as filling a capillary holder reservoir 124 with fluids such as electrophoretic buffers or luminol contained in small bottles 58 near the front of the baseplate 12.

Figure 8A:
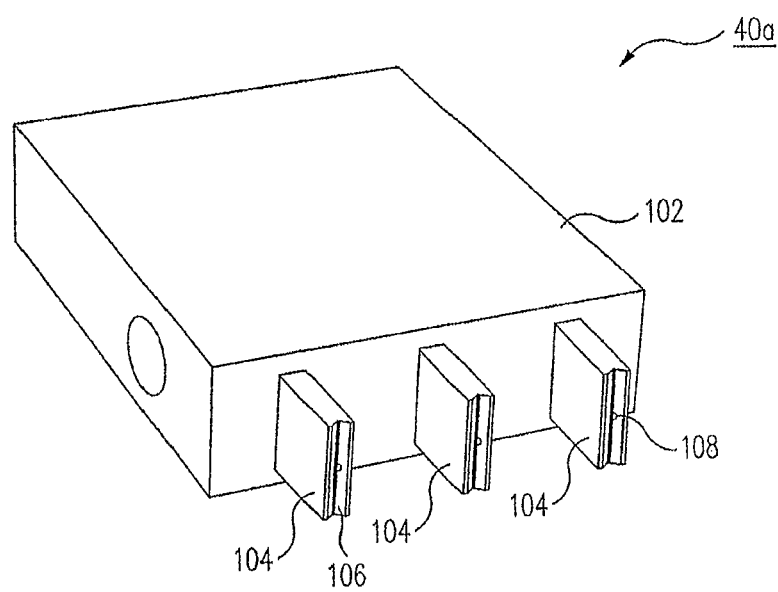
FIG. 8a is a view of a reformatting gripper.
Figure 8B:
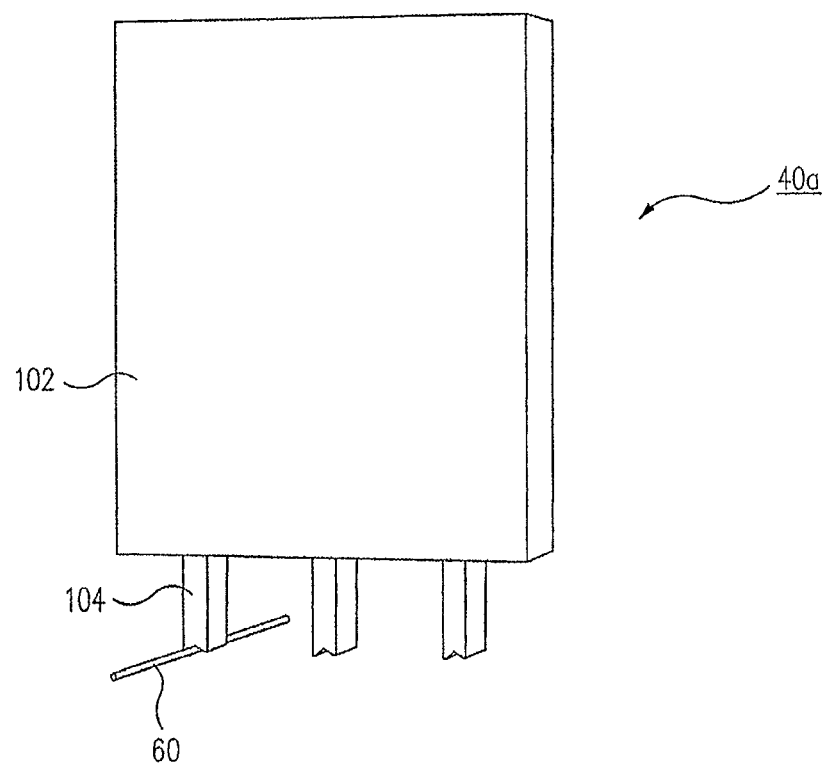
FIG. 8b is a view of the reformatting gripper of FIG. 8a holding a capillary.

The capillary reformatting gripper 40a, described more fully in FIGS. 8a-8b, performs the task of changing the spacing of capillaries between 9 mm and 2.25 mm. It is desirable to space capillaries more closely in the detection module to improve collection efficiency by creating an object area that aligns with that of the CCD detector. In the illustrated embodiment, the reformatting gripper 40a is configured to hold three capillaries on a 9 mm center-to-center spacing corresponding to that of gripper 40, although grippers capable of holding a different number of capillaries and on different spacings could also be used. As described previously, gripper 40 can place up to 12 capillaries into holders 20' and 20" on a 9 mm center-to-center spacing. Gripper 40a is then used to pick up three of the capillaries (e.g., capillaries 1,2,3) from holder 20" and place them immediately adjacent to and spaced 2.25 mm center-to-center from the other capillary positions of the capillary holder 20' (e.g., capillary positions 1,4,7). This process is repeated three more times so that all capillaries are interlaced to a 2.25 mm center-to-center final spacing as FIG. 3e illustrates. Other spacings and configurations are also possible.

The gripper 40, which will be more fully described below, is moved under computer-control to the capillaries which are to be picked up and processed (e.g., loaded with sample) or moved to another operation in the system. The gripper 40 can be programmed to pick up one capillary at a time or a number of capillaries simultaneously, such as a row of capillaries, from the capillary staging rack 30. In this embodiment, the gripper can then dip the lower end of the capillaries into a row of corresponding microwells simultaneously or each capillary in succession into a single microwell to completely fill each capillary in the gripper by capillary action or by vacuum applied to the upper end of the capillary. Each capillary has thus functioned as a volumetric pipette where the volume contained corresponds to the volume of the capillary lumen. By filling a number of capillaries from a single microwell maximum utilization can be made of fluid, conserving expensive reagents.

In some embodiments, system 10 includes a wash trough 56 which is filled either by pipette 52 from a bottle 58, or directly from syringe pump 50 and is used to wash the capillaries or the pipette tip. In the illustrated embodiment the lower end of all twelve capillaries held by the gripper can be inserted into the wash trough at the same time. At the far end of the wash trough 56 is a small well which is separate from the main fluid compartment of the trough. This small well can be used for mixing small amounts of fluids to minimize fluid consumption during use of the system. As previously mentioned, capillaries may also be washed while positioned horizontally in a capillary holder 20' by electrically pumping fluid contained within reservoirs 124 of the holder.

Figure 3A:
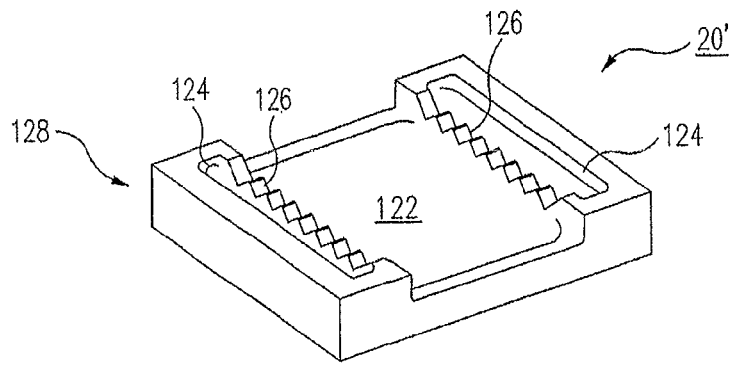
FIGS. 3a, 3b, 3c and 3d illustrate capillary holders constructed in accordance with the principles of the present invention.
Figure 3B:
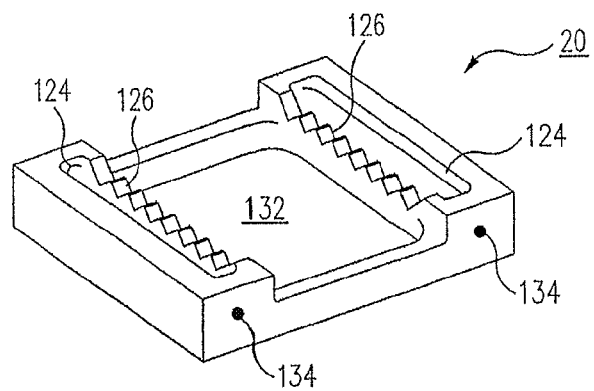
Figure 3C:
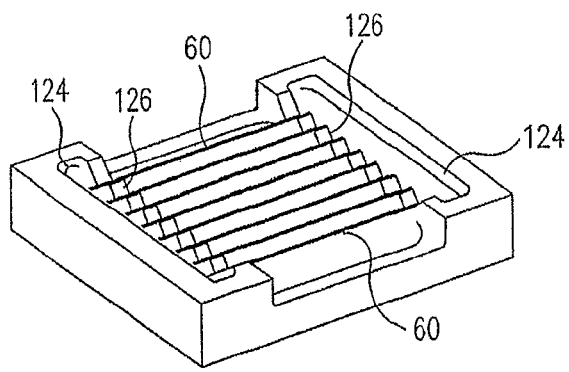
Figure 3D:
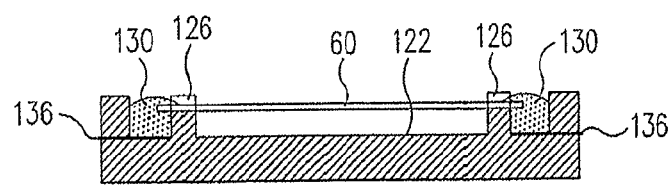
Figure 3E:
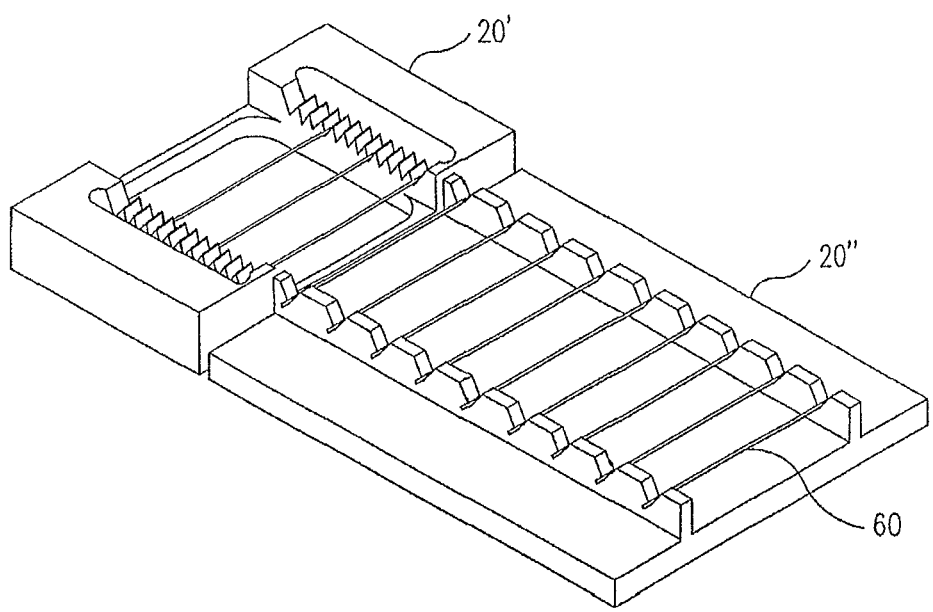
FIG. 3e illustrates an intermediate holder for use with a reformatting gripper.

FIGS. 3a-3e illustrate various embodiments of a capillary holder of the present invention. The capillary holder 20' of FIG. 3a is preferably made of a non-wetting material such as Teflon® or a rubber-like material to take advantage of fluid surface tension. On opposite ends of the capillary holder are fluid reservoirs 124. In the illustrated embodiment these fluid reservoirs extend continuously for the length of the holder. However in a constructed embodiment it is alternatively possible to subdivide the reservoirs 124 into separate compartments so that different capillaries in the holder can be isolated from one another. This would enable individual control or monitoring of each capillary as well as the ability to utilize different fluids. The central area 122 of the holder 20' is recessed so that capillaries may be gripped and deposited and removed from the holder. The inner walls of the reservoirs 124 are formed on one side as a series of V-grooves 126 which retain capillaries. The series of V-grooves 126 are deep enough that whenever a capillary is deposited into the V-groove it will automatically drop into a position defined by a V-groove 126. The back surface of the capillary holder 20' (not visible in this illustration) has two electrodes 134 extending from the back side of the holder, each of which protrudes through the wall of the holder and into a reservoir 124. These electrodes are used to apply a potential through the fluid in the capillaries for electrophoresis and isoelectric focusing. Capillary holders may be removed from the system for cleaning if required.

FIG. 3b shows one embodiment of a capillary holder 20. In this embodiment, instead of a central recessed area, the central area 132 of the holder 20 is open. This opening 132 allows the holder to be placed over a CCD detector to acquire photons emitted from substances inside the capillaries. With the embodiment 20' of FIG. 3a the capillaries are opposed to a CCD detector located above the capillaries. With the embodiment of FIG. 3b the CCD detector can approach the capillaries from either above or below. Placing the CCD above the capillary holder has the advantages of enabling visualization of the substantial full length of capillary and eliminating the possibility of any liquid spilling onto the CCD or imaging optics. In the view of FIG. 3b the electrodes 134 extending from each reservoir 124 can be seen on the front side of the capillary holder.

FIG. 3c shows the capillary holder 20' with eight capillaries 60 located in the V-grooves. The number of V-grooves, and hence the number of capillaries that can be held in a holder, is a matter of design choice.

FIG. 3d is a view of a cross section of a capillary holder of the preceding embodiments. In this embodiment the electrodes 136 extend to and through the lateral sidewalls of the reservoirs 124. The reservoirs 124 are shown filled with a fluid 130. The fluid 130 in each reservoir is seen to be higher than the lowest point in the V-grooves 126 where the capillary 60 is supported. When the capillary is placed in the V-groove 126 it breaks through the surface tension of the fluid 130 in each reservoir, which completely immerses the aperture at each end of the capillary 60 in fluid. However, because of the non-wetting material of the holder and capillary 60, the surface tension of the fluid 130 is not disturbed to a degree that would cause the fluid to leak into the central area 122 of the capillary holder. The fluid path of the capillary 60 remains in fluidic contact with the fluid 130 in each reservoir (and therefore with the electrodes 136) without any need for a physical seal by virtue of the surface tension of the fluid 130. This is particularly advantageous since there are no moving parts to wear out and making temporary seals to multiple small capillaries can be complicated and expensive to implement. In addition, this approach is significantly more scalable. For continuous chemiluminescent detection as described above, the height of the luminol fluid in one reservoir is higher than the fluid level in the other reservoir, enabling the luminol to flow through the capillary 60 from one reservoir to the other by hydrodynamic flow.

FIG. 3e shows intermediate capillary holder 20" with a capacity of twelve capillaries 60, along with a capillary holder 20' according to one embodiment. The nine capillaries located in the intermediate holder 20" may be repositioned by reformatting gripper 40a into capillary holder 20' as previously described by picking up three capillaries at a time from holder 20" and placing them in an interlaced sequence in the holder 20' until the holder 20' is filled.

In the embodiments described above, capillaries are held in the capillary holder V-grooves by gravity. In another embodiment, capillaries may be secured in the capillary holder (e.g., mechanically or by vacuum). This may be desirable as a means to prevent static charge on the capillaries or any other surface, causing the capillaries to not rest properly in the capillary holder V-grooves. Alternatively, the capillaries may be coated with an antistatic material, or an ionizing source may be incorporated into the system to prevent static charge.

Figure 4:
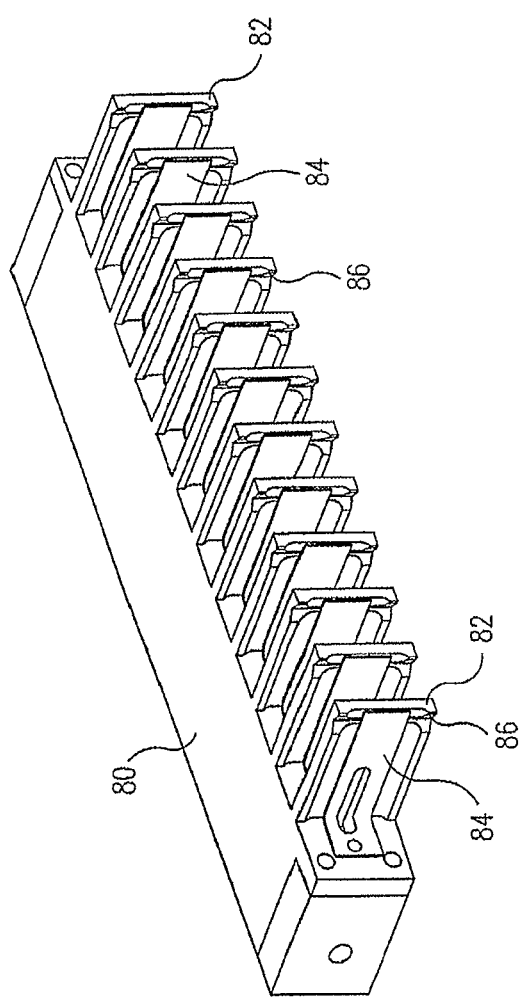
FIG. 4 illustrates a capillary gripper suitable for use in the immunoassay system of FIGS. 1 and 2.
Figure 5:
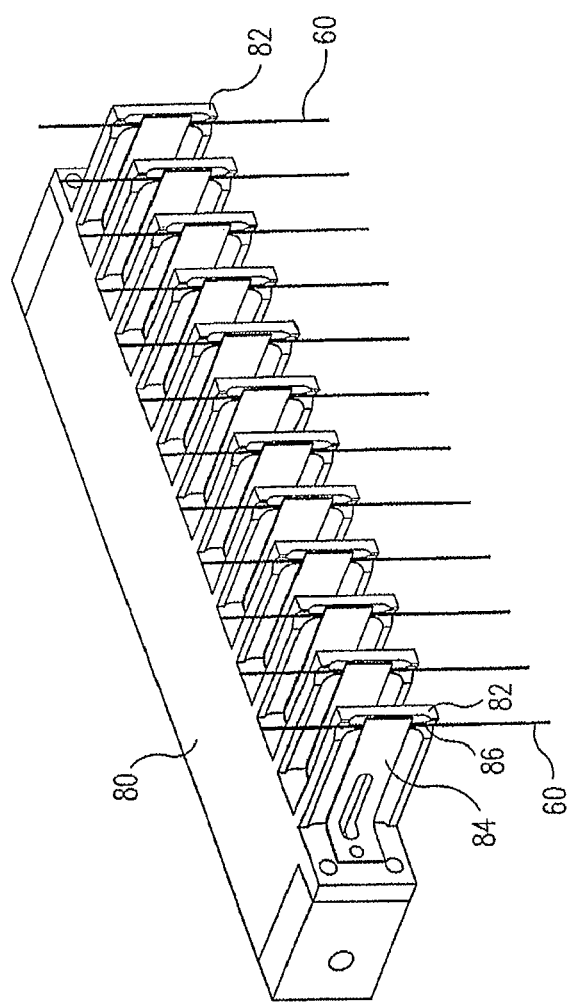
FIG. 5 illustrates the capillary gripper of FIG. 4 when holding twelve capillaries.
Figure 6:
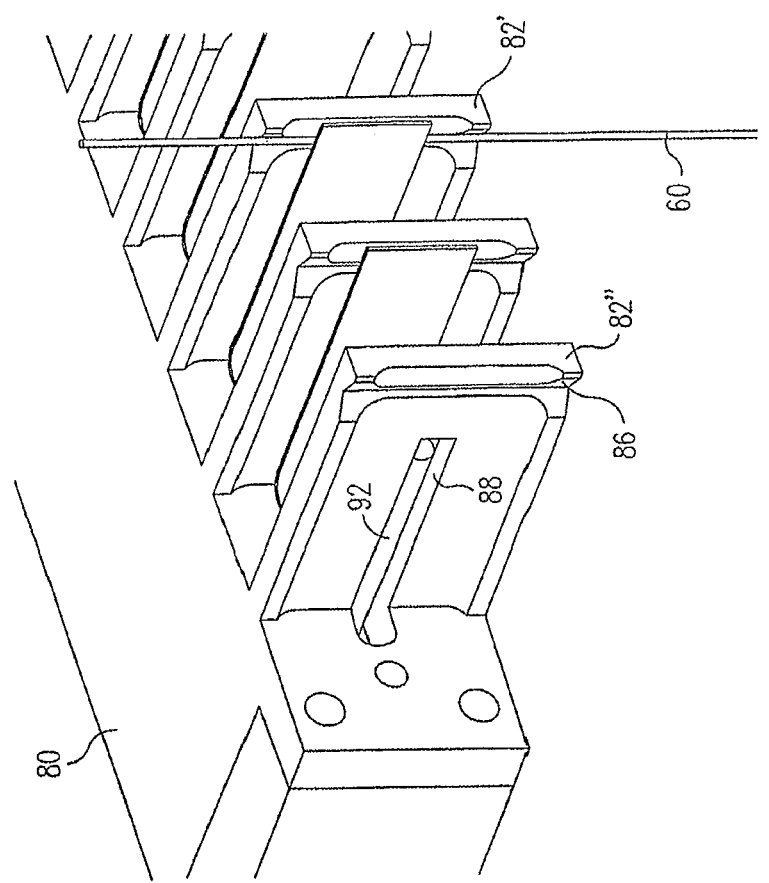
FIG. 6 is an enlarged and cutaway view of the capillary gripper of FIG. 4.

An embodiment of a capillary gripper 40 is shown in FIGS. 4-7. The gripper of FIG. 4 is configured to hold twelve capillaries on a 9 mm center-to-center spacing, although grippers capable of holding different numbers of capillaries and with different spacings can also be configured. The gripper of FIG. 4 comprises a body 80 from which twelve, fingers 82 extend. Near the distal end of each finger 82 is a groove 86 in which a capillary can be captured. The groove is normally covered by an L-shaped spring clamp 84. In their unflexed state, shown in FIG. 4, the spring clamps 84 cover the grooves 86, thereby holding capillaries in the grooves 86 of the fingers. When a gripper is to be opened to pick up or release a capillary a clamp actuator inside the body 80, described below, is actuated to flex the distal ends of the spring clamps 84 away from the fingers 82, thus exposing the grooves 86 and releasing any capillary held in a groove. In the embodiment shown, the clamp actuator for the spring clamps actuates to flex all of the spring clamps to an open position simultaneously. Alternatively, the clamp actuator can be arranged to individually open only selected spring clamps of the gripper. After the force of the clamp actuator is released the spring force of the spring clamp(s) returns the spring clamp(s) to the closed condition. FIG. 5 illustrates the gripper of FIG. 4 when holding twelve capillaries 60. FIG. 6 is an enlarged view of the fingers 82 in which one finger 82' is holding a capillary 60 and the end finger 82" is shown with the spring clamp removed, revealing a slot 88 in the finger which contains a pin 92 of the clamp actuator. When the clamp actuator is actuated to open a spring clamp, the pin 92 moves out of its slot 88 toward the spring clamp of the finger, thereby pushing the spring clamp away from the distal end of the finger where the groove 86 is covered.

Figure 7:
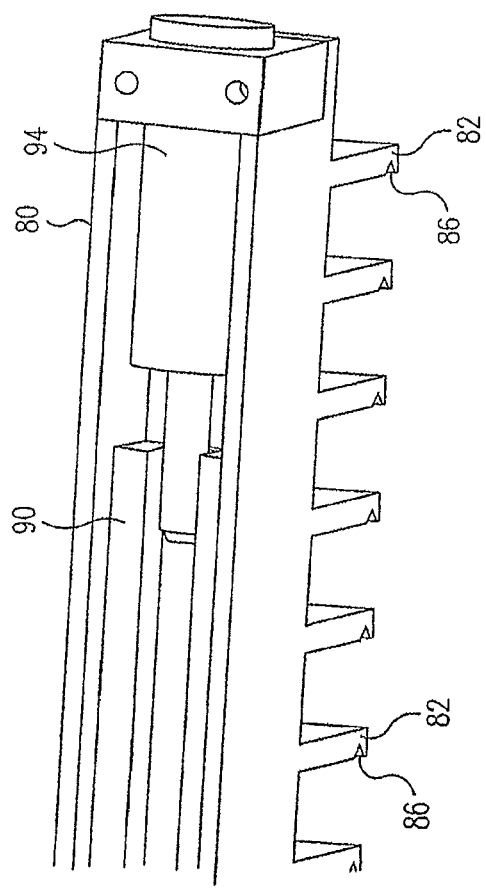
FIG. 7 is a view of the actuator mechanism of the capillary gripper of FIG. 4.

FIG. 7 is a rear view of the gripper body 80 which illustrates the clamp actuator 90. The fingers 82 can be seen extending from the opposite side of the body at the bottom of the drawing figure. The pins 92 in each of the fingers are connected to the clamp actuator 90. The clamp actuator 90 is coupled to an air cylinder 94. When air pressure is applied to the air cylinder, the piston of the air cylinder pushes the clamp actuator to the left, which pushes the pins 92 against the spring clamps 84 and opens the gripper fingers. When air pressure is removed the spring clamps close. In another embodiment; vacuum can be used to pull the air cylinder and the attached clamp actuator to the open position. An advantage of using vacuum or negative air pressure is that the same vacuum source can provide vacuum for the lid remover as well as other pneumatic actuators within the system. By choosing the appropriate pneumatic mechanism, all four tools on the robotic actuators, the capillary gripper 40, capillary reformatting gripper 40a, the pipette 50 and the lid remover 54, can be automatically operated from a common pressure or vacuum source.

As an alternative to the air cylinder an electromagnetic solenoid can be used to move the clamp actuator 90. A single solenoid can be used to move a unitary clamp actuator connected to all of the pins 92 of the gripper, or individual solenoids can be used for each pin to permit separate operation and control of each capillary gripper finger.

Figure 9:
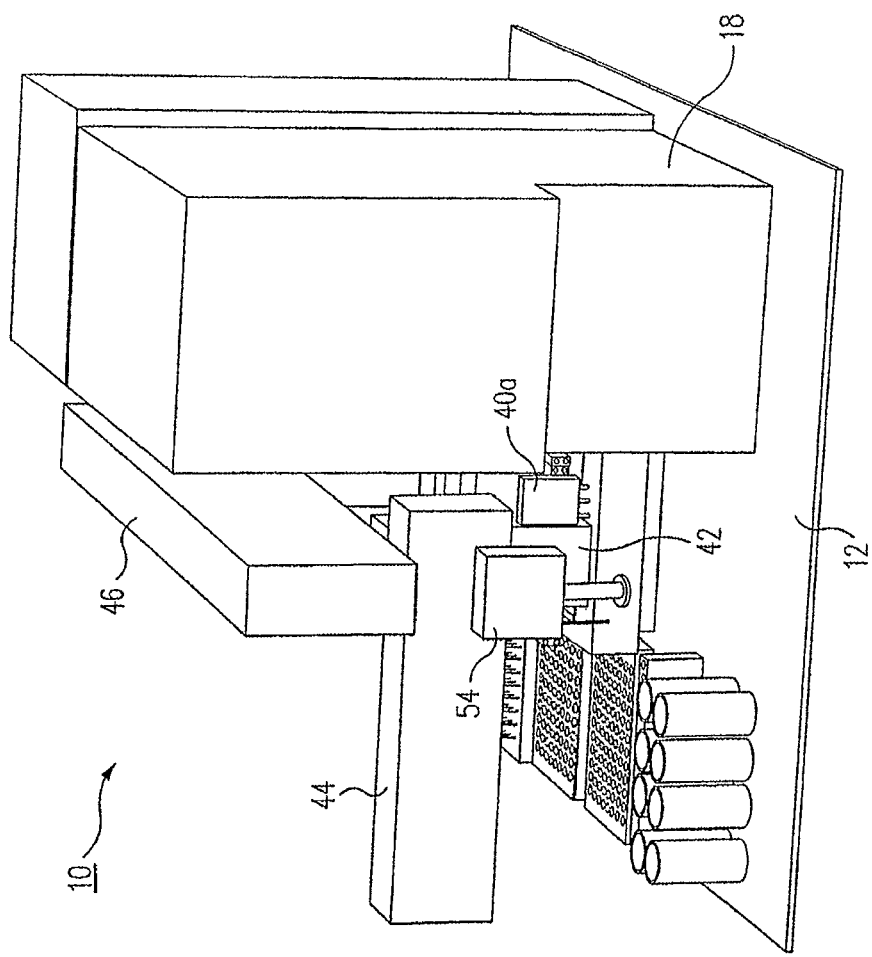
FIG. 9 is a side view of the immunoassay system of FIG. 1 showing the reformatting gripper on a system actuator.

FIGS. 8a and 8b illustrate a reformatting gripper 40a that is comprised of a body 102 from which three thin fingers 104 extend. At the distal end of each finger is a groove 106 in which a capillary can be captured. At the bottom of each groove is a small hole 108 that is connected through a valve to a vacuum source. When the gripper 40a is positioned such that a capillary is engaged in the groove 106 at the end of a finger 104 and vacuum is applied, the capillary will be captured in the groove as shown in FIG. 8b and therefore movable to a new position before release by removal of vacuum. Gripper 40a is capable of spacing capillaries more closely than possible with the design of gripper 40 by virtue of the end capture feature although capillaries are not held as securely. FIG. 9 is a view of system 10 which shows a reformatting gripper 40a located on actuator 42.

Figure 10A:
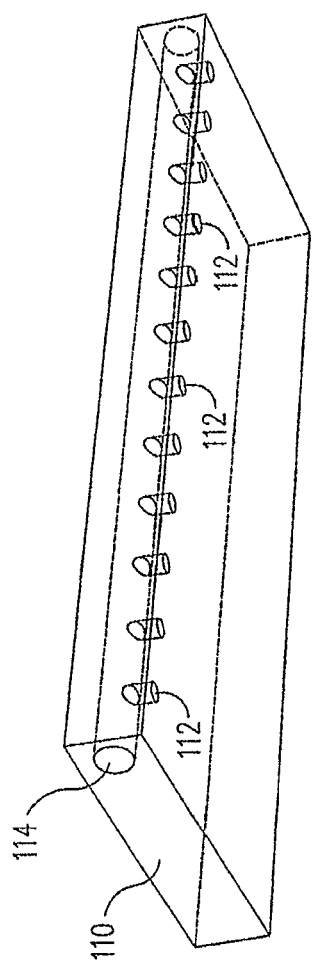
FIG. 10a is a view from below of a vacuum manifold.
Figure 10B:
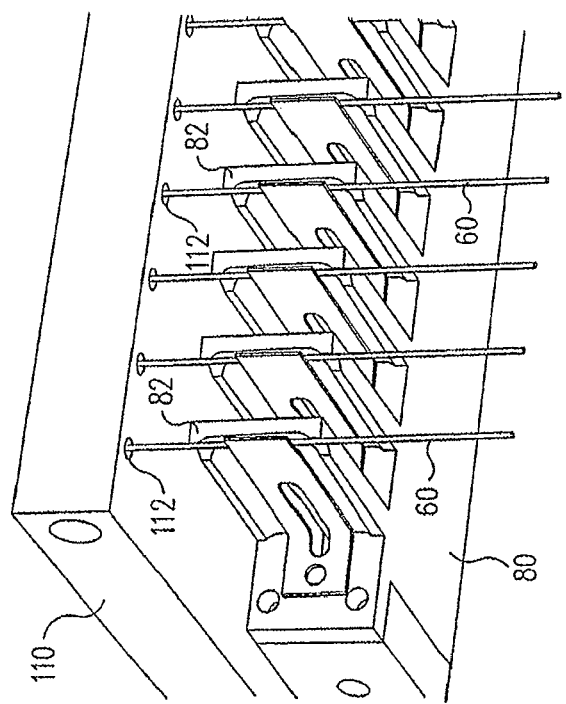
FIG. 10b is a view from below of the vacuum manifold of FIG. 10a engaged with capillaries.
Figure 10C:
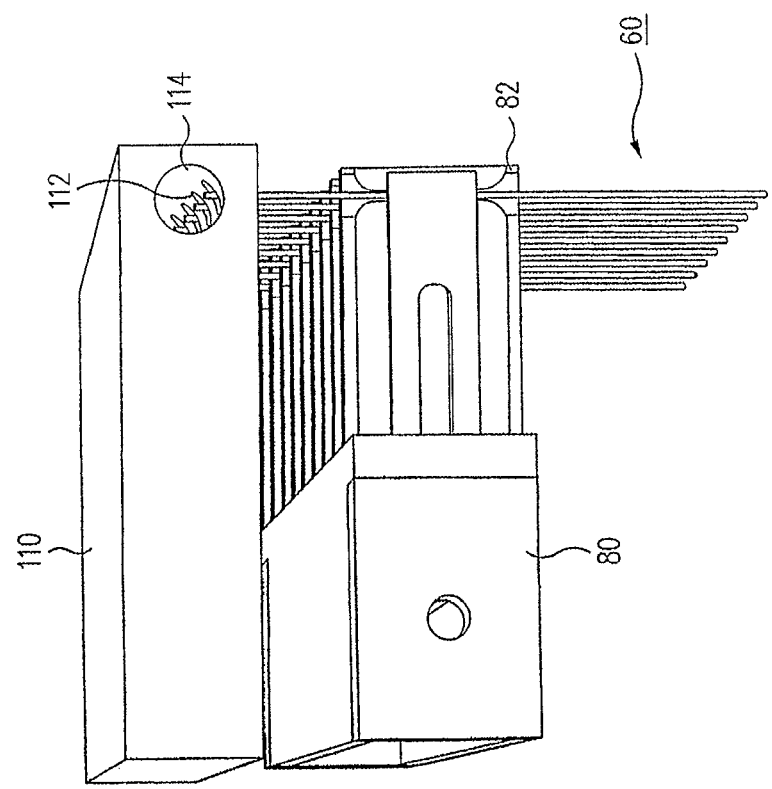
FIG. 10c is a side view of the vacuum manifold of FIG. 10a engaged with capillaries.

FIGS. 10a, 10b and 10c show a vacuum manifold 110 that may be used in conjunction with gripper 40. The manifold engages the upper end of each capillary through ports 112 such that vacuum may be applied to the upper end of each capillary and cause fluid flow up through each capillary. The manifold 110 may contain a vacuum chamber 114 common to all ports or isolated vacuum ports for individual capillaries, depending on the degree of control required. The capillaries engage the vacuum ports loosely such that when vacuum is applied, some air may flow around the outside of the capillaries and into the ports at a velocity great enough to sweep away any fluid droplets formed at the capillary ends. The total flow capacity of the vacuum source is selected so that the flow around the capillaries does not adversely affect the vacuum level at the ends of the capillaries. The rate of flow may be varied by adjusting the level of vacuum. With the lowest level of vacuum, there is only enough pressure to assist filling the capillaries without causing continuous flow. At higher levels of vacuum, which may cause droplets to be formed and swept away, the applied vacuum may be adjusted to vary the rate of flow. The vacuum may also be pulsed to cause intermittent flow conditions, such as on and off or high and low, which can be important for specific processes or reduced fluid consumption.

In an alternate embodiment, where electrical pumping of fluid (e.g., electrophoresis) is employed, the capillary may physically engage the manifold port (e.g., by a light friction fit through a hole in a membrane) to achieve a low pressure fluidic seal. Buffer is added to the region above the capillary such that an electrical connection is made from the capillary to an electrode integrated into the manifold. An array of electrodes in microwells or other fluid containers adjacent to the far ends of the capillaries completes the electrical path for pumping fluids from the wells of a microwell plate 24 or trough 56 through the capillaries. A computer controlled power supply provides the necessary control.

In another embodiment, fluid may be pumped through the capillaries by pressure.

In yet another embodiment, flow can be caused by wicking, blotting or evaporating fluid from one end of a capillary while the other end is in contact with liquid or air.

In still another embodiment, fluid can be pumped through the capillaries from a reservoir 124 while they are positioned in a capillary holder 20' (described below) by application of voltage across electrodes 136.

Preferably, system 10 is computer controlled and operated by a separate computer with programs and interfaces to control and operate the mechanisms of the system 10, in particular the robotic actuators 42, 44, 46, the capillary gripper 40, capillary reformattor 40a, the pipette 50, the lid remover 54, the computer-controlled power supply and UV light inside the separation and immobilization module 18, and the CCD array detector and light emitting diode array inside the detection module. In addition, the movable trays for the capillary holders 20', 20" and capillary staging rack 30 may also be moved under computer control.

In use, according to the illustrative embodiment the system operator will begin by placing all reagents and capillaries into the instrument, then selecting an operating protocol containing the processing steps to be carried out. The operator will also enter parameters which define particular features such as the locations of fluids which are to be accessed, where the fluids are to be mixed, voltages for electrophoresis and isoelectric focusing and the like. The steps of the operating protocol can be precisely defined because a capillary precisely defines the amount of fluid and substances needed for a process by the internal volume of the capillary. A typical protocol may begin by pumping wash fluid from bulk bottle 14 into the trough 56. The robotic actuators 42, 44, 46 move the pipette 52 to a position above solution bottle 58, lower the pipette to immerse the tip into the solution, and the syringe pump is computer actuated to withdraw a predetermined amount of solution from the bottle. The pipette is then lifted by the robotic actuators, moved above capillary holder 20' of the separation and immobilization module, then lowered at which point the solution is dispensed into one of the capillary holder reservoirs 124 to fill the reservoir above the bottom level of the V-grooves 126. The pipette is then moved to another bottle 58 where a predetermined amount of solution is withdrawn by the syringe pump and dispensed into the other reservoir 124 in capillary holder 20'. A typical processing solution may be an electrophoretic buffer. The pipette is then moved to the wash trough and the tip is washed.

Capillaries are taken from the storage rack 28 by the capillary gripper 40 and placed in the capillary staging rack 30. The capillaries are now at a known, uniform height for further handling by the gripper.

The system then acquires samples for analysis. This process may begin with the robotic actuators 42, 44, 46 moving the lid remover 54 over a covered microwell plate and removing the cover. The robotic actuators then move the capillary gripper 40 to the staging rack 30 where the gripper picks up a number of capillaries 60. The capillaries are moved to a position above the uncovered microwell plate 24 and the robotic actuators lower the gripper so that the ends of the capillaries are dipped into the fluids in a number of microwells. Each microwell may contain a sample to be analyzed. The samples are typically cell lysates containing proteins. When the end of a capillary touches a sample solution the fluid wicks up into and fills the lumen of the capillary with the sample solution. The capillaries are then lifted and the lid is replaced on the microwell plate. Next, the gripper with the filled capillaries is moved up and over the capillary holders 20' and 20" and then pivoted so that the capillaries 60 are positioned horizontally. The gripper then is lowered to place the capillaries into the V-grooves of the capillary holders. Finally, the capillaries are re-formatted to a 2.25 mm center-to-center spacing, by the gripper 40a, into the capillary holder 20' which is then retracted into the separation and immobilization module 18 by the movable tray 19 of the module.

When the capillary holder is moved into the separation and immobilization module 18, a computer-selected voltage is applied across the fluid path of the capillary, establishing a pH gradient in the capillary which separates and distributes the target molecules inside the capillary by isoelectric focusing. Once the target molecules have been separated they are bound at their locations in the capillary by photoactivation with UV light. Visible light, thermal, chemical activation or other means of immobilizing proteins (or other molecules, substances, etc.) may also be employed in which case an activating mechanism other than the UV light may be utilized in the separation and immobilization module. The binding may be covalent or non-covalent such as by hydrophobic or ionic interaction. After the target molecules have been bound in place in the capillary the movable tray moves the capillary holder out of the separation and immobilization module and the re-formatting gripper 40a positions the capillaries on 9 mm centers in capillary holders 20' and 20" for pickup by gripper 40.

In an alternative embodiment the target molecules are separated by size using a capillary filled with a polymer matrix.

The capillary gripper 40 then removes the capillaries from the capillary holders and unbound material is washed away by first dipping the lower end of the capillaries into the wash trough 56 and then applying vacuum to the manifold at the upper end to effect fluid flow. As described previously, fluids can also be moved by electrical pumping or other means. Next, the lid is removed from a microwell plate 24 containing a blocking solution, the capillary ends are dipped into the liquid in the wells and blocking solution is flowed through the capillaries. Following blocking, the capillary ends are dipped into wells containing primary antibody solution and, upon flow, binding occurs. Primary antibody may be in the same microwell plate as the blocking solution or in another microwell plate. The wash process is repeated to remove unbound antibody. As a result of dipping the capillary into the wash solution, antibody is also removed from the outside. A secondary antibody is pumped through the capillaries from yet another set of wells, binding occurs and then the capillaries are washed to remove unbound material.

Following the wash, block and binding steps described above, a luminol solution is mixed in either a microwell or in the separate well of the wash trough 56. Luminol and activator are contained in bottles 58. Pipette 52 is used to transfer the solutions from bottles 58 into the mixing well. The solutions are mixed by repeatedly aspirating and dispensing the fluid in the mixing well. To minimize the amount of luminol used, only a small amount is prepared in the selected well by carefully metering the fluid with the pipette 52. Each of the capillaries are dipped into and therefore filled with the luminol solution. The remaining prepared luminol is then transferred to one of the two reservoirs 124 of a capillary holder 20' and water is dispensed into the other reservoir 124. Since the luminol is intended to flow hydrodynamically through the capillary in order to continuously stimulate chemiluminescence from the bound antibody-target complexes, slightly more volume of luminol is injected into one reservoir than water into the other to promote the desired flow. The capillaries are then placed in the capillary holder 20' containing the luminol by the capillary gripper 40 and re-formatting gripper 40a. The capillary holder 20' is moved into the detection module 16. Inside the detection module the capillary holder is positioned with the capillaries in opposition to the CCD array detector, which in this embodiment is above the capillaries. As luminol flows through the capillaries chemiluminescence is induced and the photons produced are detected by the CCD array detector in relation to the locations from which the photons are emitted. The detected data is received by the computer and processed into a desired display which may be, for example, a graph of light intensity versus location within the capillary or bars sized and located in a row as a function of location within the capillary, much in the manner of the familiar Western blot pattern. To detect fluorescently labeled molecules within the capillaries, the capillaries are irradiated by a light source and the resulting fluorescence is detected by the same CCD array. In this way the fluorescence data may be accurately overlaid spatially with the chemiluminescence data. As an alternative to a CCD array, in such an embodiment a fluorescent scanner may be used.

Upon completion of detection, the capillaries are removed from the capillary holder of the detection module 16 and discarded into a capillary waste container (not shown) on baseplate 12.

One skilled in the art will appreciate that the above procedure is merely representative of one experimental protocol which may be performed by an assay system of the present invention. As will be explained more fully below, the system operator has the ability to add, omit, reorder, and vary the processing steps used in a given experiment.

Figure 11:
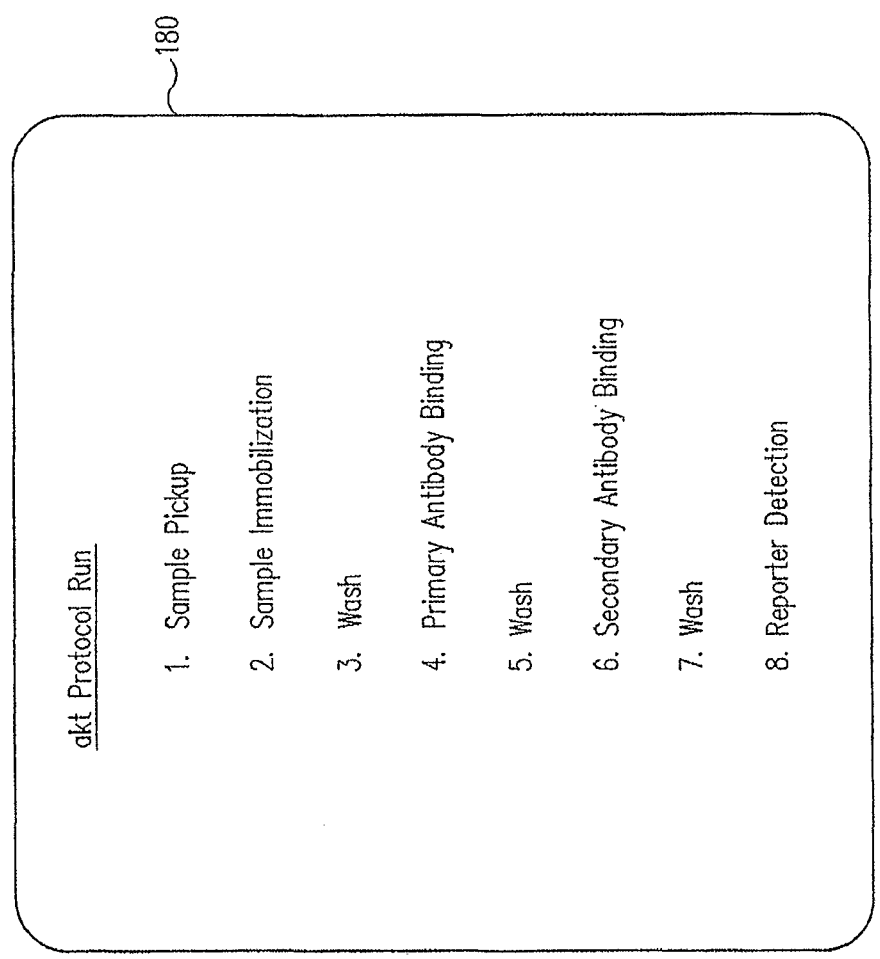
FIG. 11 is a screen shot of a graphical user interface showing an experimental protocol setup screen.

The computer system which controls the actuators, tools, power supply, UV light source, and CCD array of an immunoassay system of the present invention also preferably has a graphical user interface by which the system operator can select an operating run protocol, initialize the system, execute the protocol run, and store and analyze the results in a reliable, convenient and easy to operate manner. An exemplary embodiment of the graphical interface is described below. The graphical user interface has a means such as a menu, directory or listing by which the system operator can select default run protocols, protocols stored from previously executed runs or can prepare a custom protocol. The protocol provides a sequence of instructions to the computerized system regarding how to manipulate the reagents in order to produce the desired results. The selected run protocol may be presented on the graphical user interface as a sequence of steps, as a flowchart or other presentation of the protocol sequence. For example, FIG. 11 shows the steps of a protocol called "akt Protocol Run" presented in a textual outline of protocol steps. As will be apparent to those skilled in the art, this example illustrates a sequence of very general steps of a typical run, where a run is the execution of all of the steps of analytical process starting with reagents in microwell plates and ending with the output of analytical data. Pre-programmed protocols contain a list of rules or restrictions on what a user can and cannot do during a run. For instance one such restriction prohibits the operator from selecting a secondary antibody binding step before a primary antibody step. These rules prevent the occurrence of basic mistakes in the execution of a protocol run. For purpose of the following example a run is defined as a set of concurrent experiments performed in one to twelve capillaries.

The protocol has a number of operating conditions with parameters which may be set by the operator. To see these operating conditions the operator clicks on a step with the pointing device of the computer and a pop-up or pull-down menu appears with the operating conditions for that step. Default and previously stored protocols will have these parameters initially defined, although the operator has the opportunity to change them. For example, when the operator clicks on the "Sample Immobilization" step on display screen 180, a menu appears with choices for the immobilizing source. The operator may select "UV light," for instance. Another parameter may be "Exposure time," which the operator may enter. The operator may also need to define or redefine the voltages for electrophoresis or isoelectric focusing. Similarly, the menu which appears when clicking on "Reporter Detection" will ask the operator to define the time period for collecting photons with the CCD detector array. Protocol rules may delimit the choices or range of choices which the operator may enter or select for a given protocol.

It is also necessary to define the reagents to be used for a protocol run. A screen for doing this is shown in FIG. 12. A list of possible and previously used reagents may be displayed by clicking on a reagent type. For instance, when the operator clicks on "Ampholyte", he or she is shown a list of ampholytes previously used or defined on the system. The choices may be delimited by the rules of the selected run protocol. The operator can select a reagent from the list or enter the information from the keyboard. Reagent information may also be downloaded from the Website of the instrument manufacturer or from Websites of reagent suppliers. In this example the operator has chosen anti-AKT as a primary antibody and Anti-mouse as a secondary antibody for the run to be executed.

Figure 13:
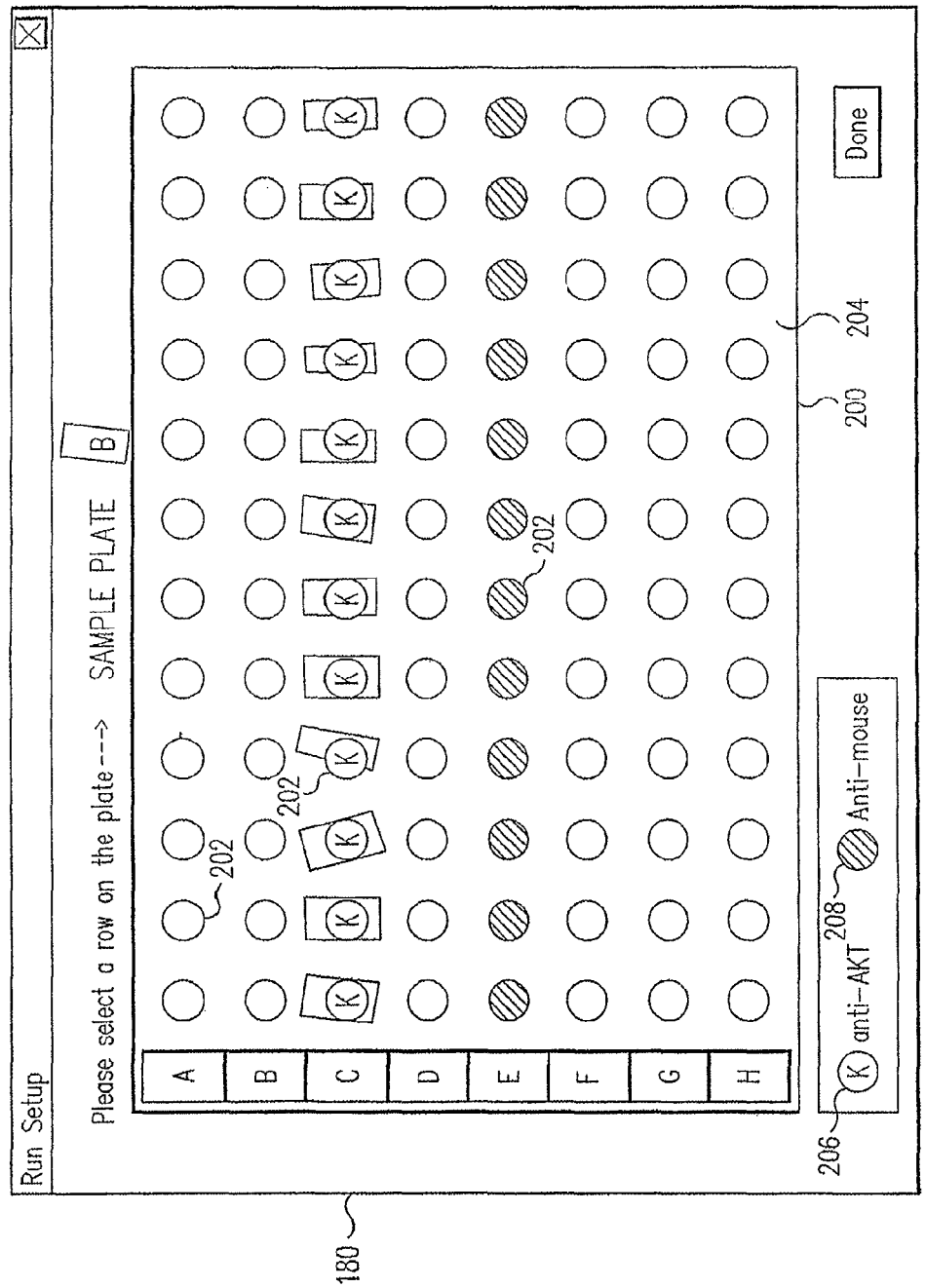
FIG. 13 is a view of the graphical user interface showing a microwell plate setup screen.

In addition to defining the reagents to be used it is also necessary to define their locations on the instrument. Before the protocol can be run it is necessary to set up the samples, reagents and capillaries in known system locations. FIG. 13 shows a graphical user interface screen 180 for the setup of a microwell plate 24. A typical instrument setup may have one microwell plate of samples such as cell lysates or proteins. A second microwell plate may be loaded with primary antibodies and a third microwell plate loaded with secondary antibodies. A fourth plate may be loaded with blocking and wash solutions. As previously mentioned each of the stations 22a-22d is visually marked. For instance, station 22b may be marked with a red color in the location on the baseplate where the microwell plate 24 is placed. This will enable the system operator to see the red color through the transparent or translucent plate material. The other stations will be marked with different graphics or colors. The graphical user interface displays a graphic 200 of this microwell plate as shown in FIG. 13. Each row of wells is delineated by a letter at the left side of the row. Clicking on the letter selects all of the wells of the particular row. If different reagents or samples are to be located in the same row it may then be desirable to select an individual well in a particular row. In this case, each column of wells is delineated by a number, enabling a specific well in the plate to be identified by a unique letter and number, much in the way a cell of a spreadsheet is addressed. The circular microwells 202 in the plate graphic 200 are presented against a background 204 which is colored the same color as the color below the microwell plate at station 22b. Thus, when the system operator is viewing the display of FIG. 13 he or she is seeing the 96 microwells 202 against a red background corresponding to the actual microwell plate over the red station color. The operator will thus immediately see that the red display of "SAMPLE PLATE B" corresponds to the red color seen through the microwell plate at station 22b, thereby reducing any confusion of the plate being viewed.

The operator highlights selected reagents on the reagent screen of FIG. 12, which causes the selected reagents to appear as choices below the plate graphic 200. The reagents chosen are those which are located in SAMPLE PLATE B at station 22b. Alternatively the operator may choose the reagents which are to be found in the microwells of this plate from a menu or by entering a reagent from a keyboard. As the reagents for SAMPLE PLATE B are selected they appear on the graphical user interface below the plate graphic 200 as shown in the drawing. Next to each reagent name is a graphic or color which the computer assigns or the operator can select. In this example the anti-AKT antibody is identified by agraphic "K" and the anti-mouse antibody is identified by a yellow color, represented in the drawing by a diagonal line pattern. When the operator clicks on the "K" graphic 206 for the anti-AKT antibody and then clicks on the letter of a row of the plate graphic, the full row is filled in with the "K" graphic, indicating that all of the microwells in that row contain the anti-AKT antibody. Alternatively, the operator may click on each microwell graphic 202 individually to mark microwells one by one which contain the reagent. This latter approach will be taken if a row contains more than a single type of reagent or some of the microwells of the row are unfilled. If the operator mistakenly clicks a "K" in a microwell graphic, he or she removes it by clicking on the microwell graphic a second time. In this example the operator then clicks on the yellow graphic 208 for the Anti-mouse antibody and on the letter "E" to mark all of the microwells of row E as containing this second antibody. The finished graphic in FIG. 12 indicates to the control computer that the microwell plate in station B has anti-AKT antibody in all of the microwells of row C and Anti-mouse antibody in all of the microwells of row E. The operator then clicks the "Done" button to indicate that the setup of SAMPLE PLATE B is complete. When a protocol step calls for one of these antibodies, the computer now knows where to send the actuator to find the needed reagent.

Right-clicking on one of the reagent graphics 206 or 208 will cause a popup message or menu to appear with the choice of "Select All Microwells." The Operator clicks OK on this menu or message and all of the microwells of the plate are marked as containing the specific reagent. The operator then clicks "Done" to finish the setup of that microwell plate.

The system can be set up to visually mark microwells which have been accessed during an experiment. After the reagent in a particular microwell has been used in the assay, its color is grayed over on the graphic. Thus, at the conclusion of the process, the operator can return to the graphic and note which microwells were accessed during the process by the microwells which are grayed out.

The operator can set up every rack and tray in this same graphical intuitive manner.

For example, the operator may desire to begin the protocol with a buffer solution preloaded in the wash trough 56. The operator calls up the wash trough graphic and selects a buffer solution which may be shown as blue on the graphic display. The operator clicks on the buffer solution graphic and clicks on the wash trough. The wash trough graphic is now displayed filled with the blue color representing the buffer solution and the computer now knows that the trough contains the buffer solution at the start of the run. In a similar manner the operator can indicate the positions in the capillary racks 28 which contain the capillaries needed for the run. For example, one rack may contain coated capillaries and another rack may contain uncoated capillaries. The operator in this way indicates to the computer where the capillaries needed for this particular protocol may be found through the graphical user interface.

After the operator has set up all of the locations of the disposables called for by the protocol, he or she may select "Setup Review." This will cause the graphical user interface to cycle through each graphic of the system stations at the touch of a button. As the user sees each graphic the relation to the physical plate or rack or container will be seen immediately by the graphic and/or its color such as the red color for SAMPLE PLATE B seen on the screen and visually identified on the baseplate 12. The operator can in this way check to see that the setup given to the computer corresponds to the exact locational setup of reagents and capillaries on the system. The computer will run a check in the background of the materials needed for the selected protocol and will inform the operator if a reagent or device called for by the protocol is missing from the setup.

The operator can view the locations of the samples and reagents to be used by the protocol with the Sample Tracking screen 180 seen in FIG. 14. After the operator defines the locations of the materials the computer will automatically populate this screen with the previously entered information. For instance, the identities and locations of the primary and secondary antibodies has been filled in on this screen from the information previously entered for SAMPLE PLATE B. The computer will use materials in a default sequence from the lowest numbered microwell containing each needed material. The operator has the opportunity to change the automatically entered selections on this screen if desired.

The run protocol of this example performs an analysis of samples in twelve capillaries of a capillary holder 20'. The Run Setup screen of FIG. 15 shows the operator the sample and reagents to be used in each capillary 1-12. If the operator wants to change a sample or reagent for a particular capillary he or she clicks on the name below the capillary number and can select another sample or reagent from the materials previously entered during the setup. The computer automatically identifies the location of a changed sample or reagent and notifies the operator if the sample or reagent is not present (i.e., the sample or reagent was not previously identified during the setup procedure.) The operator has now selected the experimental conditions for each erroneous result. The run data can be stored together with the results so that the run can be replayed if questioned in the future, and can be stored in the computer by the operator and recalled to run the same protocol at a later date. Thus, there is no need to go through the full setup procedure for commonly run protocols and locational setups; the protocol data can simply be recalled from storage to immediately populate the setup displays and run the protocol.

Figure 16A:
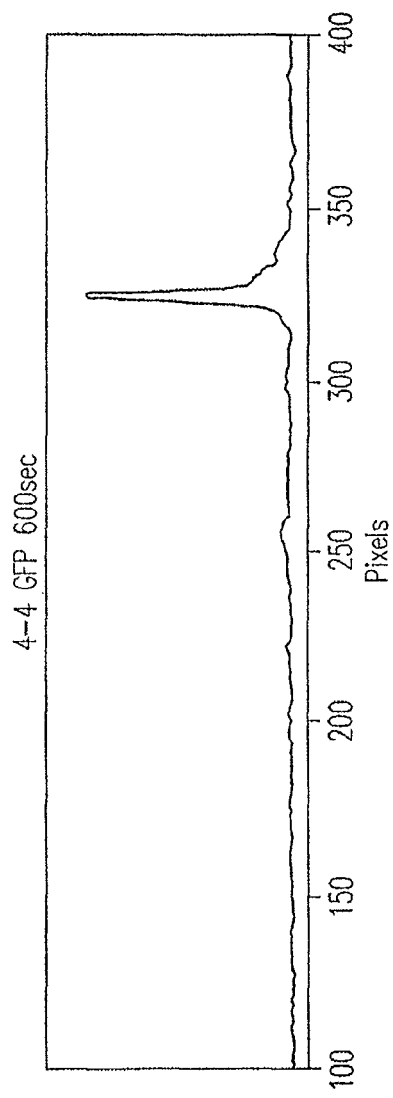
FIGS. 16a and 16b illustrate the presentation of analytical results of a capillary analysis in a graphical form.
Figure 16B:
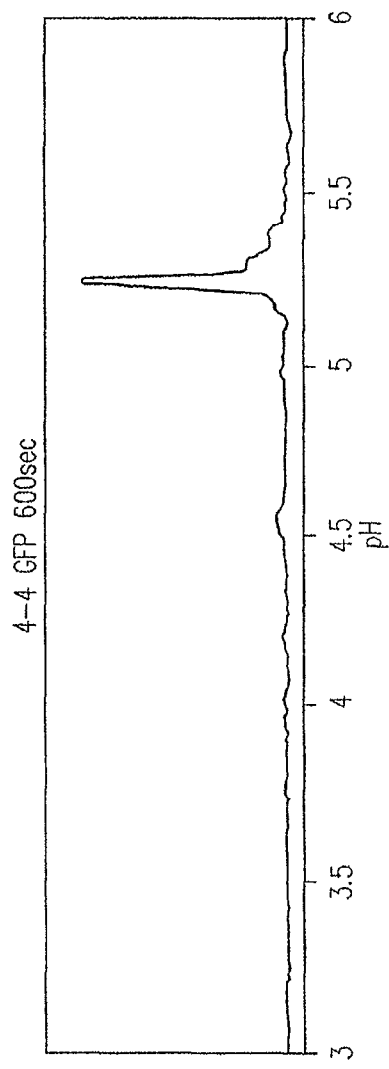

During the "Reporter Detection" step, a two-dimensional image is taken of each capillary. This image represents chemiluminescent or fluorescent light emitted from the contents of the capillary. More photons are emitted from capillary locations where more of the target protein molecules are located. Intensity and location of the emitted light is important for subsequent data analysis. There are two ways to represent this emitted light: line graph and blot image. An example of one line graph can be seen in FIG. 16A, where the X-axis is a function of the capillary locations from which photons were detected and the Y-axis is a function of the number of photons detected at each location. This line graph is analogous to the experimental results displayed by a chromatographic instrument. For all the graphs created from emitted light, a positive-going peak represents a collection of protein molecules of interest. In this example the horizontal scale of the line graph is displayed in pixels which represent the picture elements in the camera sensing device (CCD array). The line graph information is also displayed in FIG. 16*b* but with pH on the horizontal scale. The pH scale is more relevant for identifying a specific protein corresponding to a graph peak. The pH information can be displayed after a pI standard calibration is applied to the data as described more fully below. It is possible to simultaneously display multiple graphs representing the light emitted from multiple capillaries for one run. The multiple graphs can be tiled in various arrangements on one display screen to permit viewing and comparison. It is also possible to display multiple traces in one grid area using a "waterfall" technique. One skilled in the art will recognize that other embodiments are possible including one dimensional capillary images or images produced by light sensitive detectors.

In another embodiment, where the separation is by molecular weight (charge/mass ratio), the horizontal scale may display the molecular weight.

A more convenient and intuitive way of displaying emitted light from multiple capillaries is the pseudo-blot or pseudo-gel image. This image is analogous to the final result of a Western blot or electrophoretic gel. This data representation is familiar to scientists in the field of protein sample of each capillary of this protocol run.

After setup has been completed the operator can verify how the protocol will operate by selecting "Verify Protocol." When this action is selected the operator can click on each protocol step of FIG. 11 and see the operating parameter used during that step (e.g., an isoelectric focusing voltage of 300 volts is applied for 90 seconds during the separation process of the "Sample Immobilization" step.) The operator is also given the opportunity to see the graphic of each station device which will be used during the step and the change in that device during the step. For instance, when the operator clicks on the "Primary Antibody Binding" line of the display and selects "Display Stations", he or she will see the microwell plate graphic display of FIG. 13 with the plate row C highlighted by, for instance enhanced brightness or flashing which shows that the primary antibody anti-AKT of plate B was used during this step of the protocol. When the option to mark accessed microwells has been invoked, the microwells of that row will be grayed out in this display, showing that the antibodies of these microwells have now been used in the run.

It will be appreciated that the Verify Protocol action enables an operator to step through the complete protocol before the run is actually commenced so that the successful execution of each step can be checked in advance of the run. The operator can go back and change any of the setup conditions if desired and re-execute the Verify Protocol action until the desired run has been fully checked in advance. This is very useful for training new operators, who have a means for setting up a protocol and stepping through it graphically before actually committing scarce or expensive samples and reagents for an actual run. Unskilled operators can thus become comfortable with operation of the system very quickly.

Figure 17B:
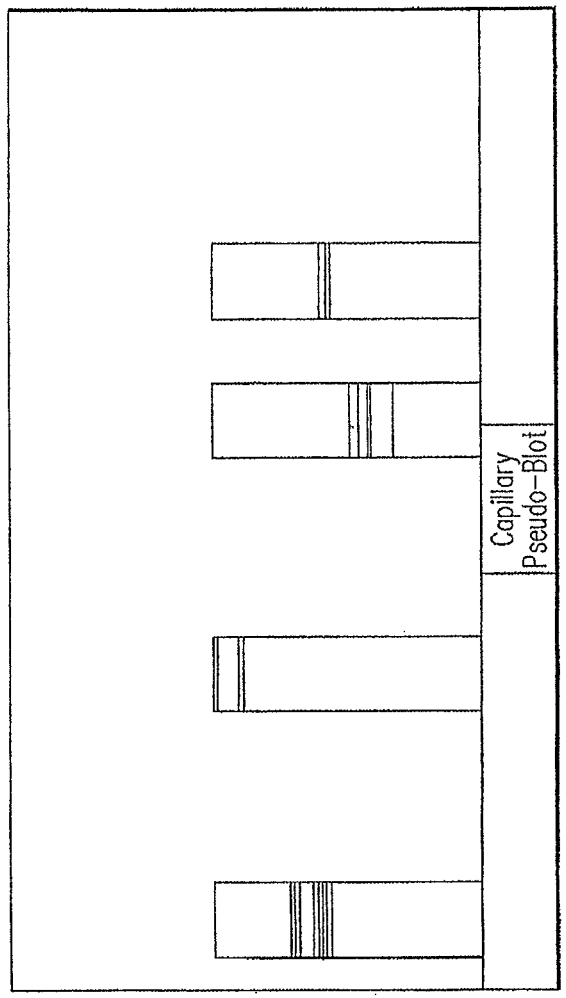
FIGS. 17a and 17b illustrate the presentation of analytical results of a capillary analysis in the form of a pseudo-gel image.
Figure 17A:
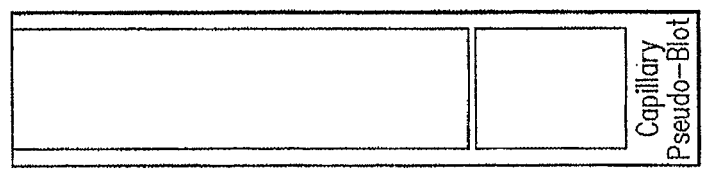

After the protocol run has been executed the computer saves all of the operating data from the run. The operator can then go back to the protocol screen of FIG. 11 and click on "Run Review." This action will cause the computer and graphical user interface to step through the protocol again in the same manner as the "Verify Protocol" action, but this time with the actual steps and actions recorded during the run. For instance, if the analytical results seem incorrect or unusual, "Run Review" can be executed to replay the protocol steps and view each parameter, reagent, sample, and location used and recorded during the protocol run. In this way the operator can look for any mistakes in setup or reagent acquisition which may have caused an research. An example of a pseudo-gel image for one capillary is shown in FIG. 17a. An example of a display of multiple pseudo-gel images is shown in FIG. 17b. The display of FIG. 17b would be useful, for instance, when a run was conducted using eight capillaries and the sample results from the eight capillaries are to be compared. In FIGS. 17a and 17b the positive-going peaks representing proteins of interest in the line graph type of display are displayed as white bands against a black background, with higher line peaks shown as brighter white bands. It is also possible to display the positive-going peaks as black bands against a white background. The choice of white or black for the bands is left to user in the form of a binary state button in the software interface. Different colors can be used in the pseudo-gel image to represent differences in the underlying chemistry. If the operator wants to overlay an image of chemical standards, where band position connotes a quantitative value, against an image of the unknown sample being studied, then different colors may be used for the standards versus the unknown for ease of comparison. Another embodiment using multiple colors is the color designation of multiple unknown chemical species in one capillary. In one embodiment this is achieved by passing multiple primary antibodies through a capillary and allowing them to attach to different and unique proteins. Then, multiple secondary antibodies are passed through the capillary that attach to the primary antibodies of choice. The secondary antibodies also have a reporter molecule that emits a unique wavelength of light when exposed to an external stimulus. When each unique secondary antibody emits a unique wavelength of light, it can be uniquely detected through an optical filter and then displayed in a computer display with a unique color.

Figure 18:
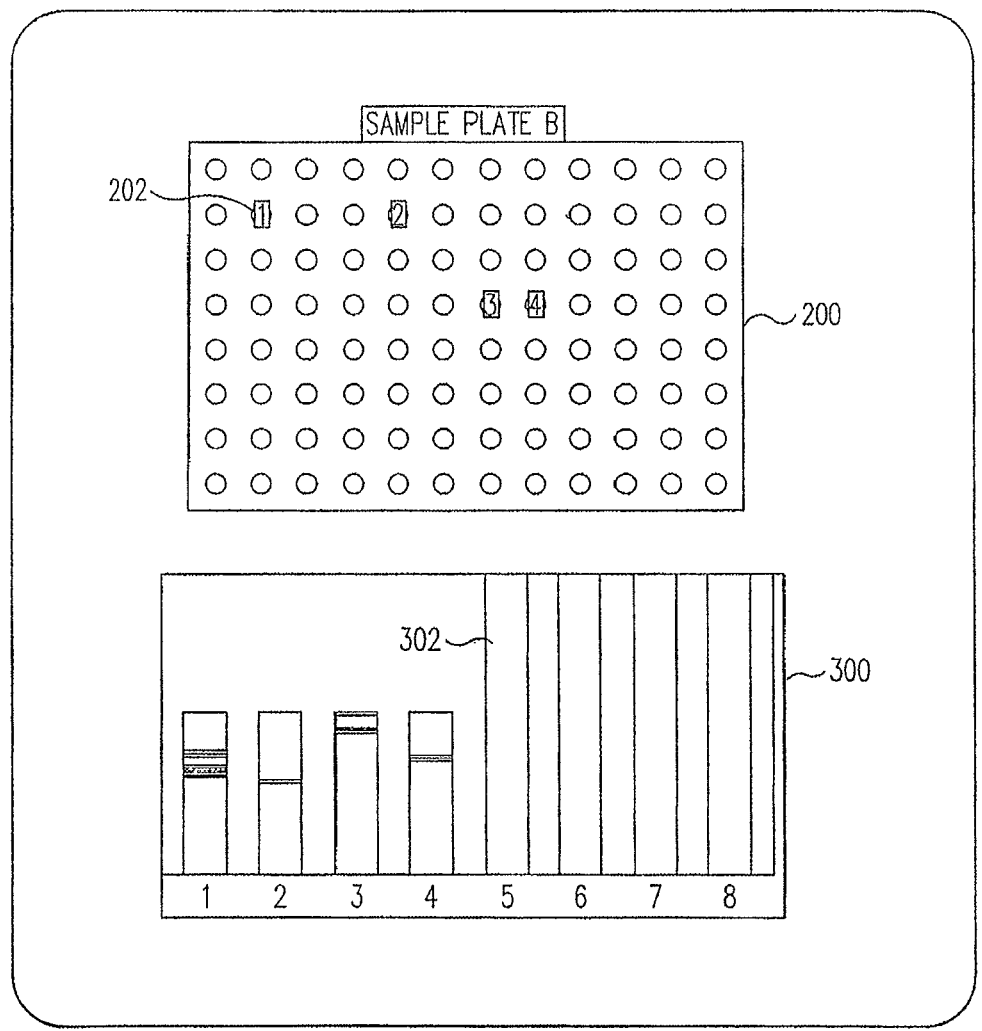
FIG. 18 is a screen shot of a graphical user interface showing the ability to graphically construct a pseudo-gel image of a selected set of sample analyses.

An advantage of the pseudo-gel display technique in an automated assay system of the present invention is the ability to present a multiple band display of selected results from different capillaries of a run or from different capillaries of different runs. Since the stored experimental results identify the location of each microwell which was the source of each experimental sample, the microwell plate graphics can be used to selectively display the experimental results of desired samples in the familiar side-by-side band format. For example, FIG. 18 illustrates a display screen shot of microtiter Sample Plate B 200 on the same display screen as an eight column pseudo-gel display 300. Initially, the columns of the pseudo-gel display 300 are empty, as shown by empty columns 302 in positions 5-8. In this example the microwells of Plate B contained samples which have been analyzed by the system and the results stored. When the system operator manipulates his graphical pointing device to a microwell of the plate, the identity of the sample which was contained in the microwell appears on the screen, as by a small tool tip box appearing next to the screen cursor. When the operator is pointing at a microwell of a sample that he or she wants to display in the pseudo-gel display, the operator "drags" the sample from the microwell to a particular empty column of the pseudo-gel display. When the operator releases the dragging action the results of the analysis of that sample appears in the indicated column and the column number in the pseudo-gel display 300 appears over the microwell of the plate image 200 which was the source of the sample. In FIG. 18, for instance, it is seen that the results in column 1 of the pseudo-gel display 300 are of the sample which came from microwell 202 in the second row, second column of the plate 200. It is seen that the results in the second, third and fourth columns of the pseudo-gel display 300 came from other indicated microwells of the plate 200. If desired a tabular legend can be displayed which relates the sample name and location to the pseudo-gel image columns. It will be appreciated that this ability to create a pseudo-gel image of any group of results enables a familiar, customized blot image to be created of the results of any set of sample analyses and in any sequence in the pseudo-gel display 300

A user of this system ultimately wants to associate quantitative information with the images that have been displayed. The two most important attributes of the bands shown in FIGS. 17a and 17b are protein identification and quantity of protein. Protein identification is accomplished by a combination of primary antibody selection and alignment relative to a known pH/pI standard. The primary antibody used should have a relatively high affinity for the protein of interest. This selection however may not be sufficient to uniquely identify the protein due to its tendency to attach to other proteins. More precise identification requires knowledge about the isoelectric point (pI) of the protein. To accomplish this, a series of pI standards is placed in each capillary. These standards migrate to various pI points during the isoelectric focusing step. The standards then emit light either via fluorescent or chemiluminescent means. The image of pI standards is compared to the image of the protein bands. Based on the standards located closest to the protein bands, the analytical software in the computer can infer a pI value for the unknown band. This pI value is then compared against known historical pI information for the protein of interest. If the pI matches the historical data within some small variation, then the protein can be positively identified. If the pI value does not match then the band was created by a different protein molecule that the primary antibody attached to it. Another method for separating and identifying protein molecules is to use molecular weight, also known as size. If unknown proteins were mixed with size standards and then separated on the basis of size, then the unknown proteins can be compared with the standards to perform a positive identification. One skilled in the art will recognize embodiments where the means of separation of the standards required are different such as molecular weight, hydrophobicity, anion/cation characteristics, affinity, and others.

Protein quantity can be determined by comparing the amplitude of an unknown protein band with the amplitude of a known quantity of protein. The amplitude measurement is made by summing all of the pixel amplitudes representing emitted light in a given protein band. A series of known protein quantities can be placed in multiple capillaries and the band amplitudes can be determined and saved for future amplitude comparisons.

When the analytical software has made a determination of protein identification and quantity the system can display that data alongside the line graph display, pseudo-gel image or in a table. An example of an annotated pseudo-gel image is the one with an identified AKT Phospho-12 ng/mL band at the right side of FIG. 17b.

Most analytical systems present output data in a format that is native to the detection scheme of the instrument. For instance, HPLC and capillary electrophoresis detection systems generate data over a period of time. Hence the data for these instruments is presented as a plot of signal versus time. In separation systems such as slab gels or TLC plates, where it is the separation of materials at the end of a period that is of significance, the separation data, when plotted, is plotted as a function of distance. However the variables of time and distance are not those that are of primary concern to the experimenter. Rather, the experimenter is interested in one or more properties of his chemical unknown, such as the pI length of a DNA fragment in nucleotides or the isoelectric point of a protein in pH units. This will usually require the experimenter to separate compounds with known properties in the same separation system, then construct a curve of mobility or migration or retention time vs. the property of interest. This translation table allows the experimenter to use the time or distance value generated by his instrument for his unknown analyte to look up the chemical parameter in which he is interested.

The difficulty with this two-step approach is that it leaves the experimenter with chromatograms or electropherograms that are one step removed from the data that he wants to analyze. In accordance with a further aspect of the present invention the assay system applies the calibration data from separation standards to the chromatogram or electropherogram and displays the analytical data as a signal versus the desired coordinate system. This effectively transforms the signal versus time or distance plot into a plot that is immediately useful to the experimenter, as it is quantitated in coordinate values which are meaningful to his experiment. This technique can be used in any separation system where the retention time, migration time, mobility, or distance traveled is a function of some physical variable in the analyte, such as DNA chain length or pI, and when chemical standards are available to calibrate the separation system.

Figure 19:
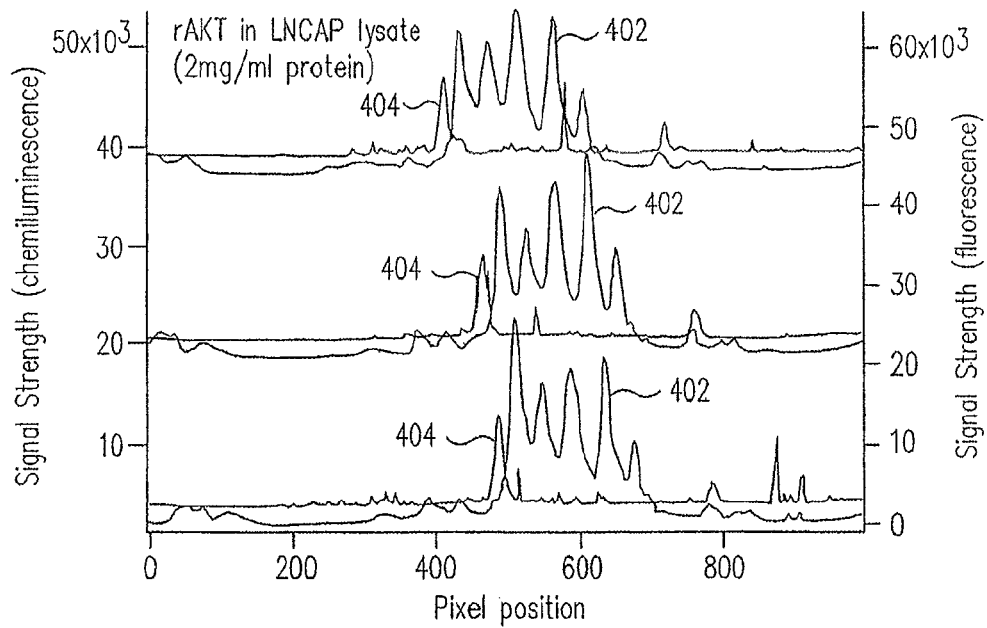
FIG. 19 is a graph of the fluorescents and chemiluminescence signal extracted from 3 capillaries.
Figure 20:
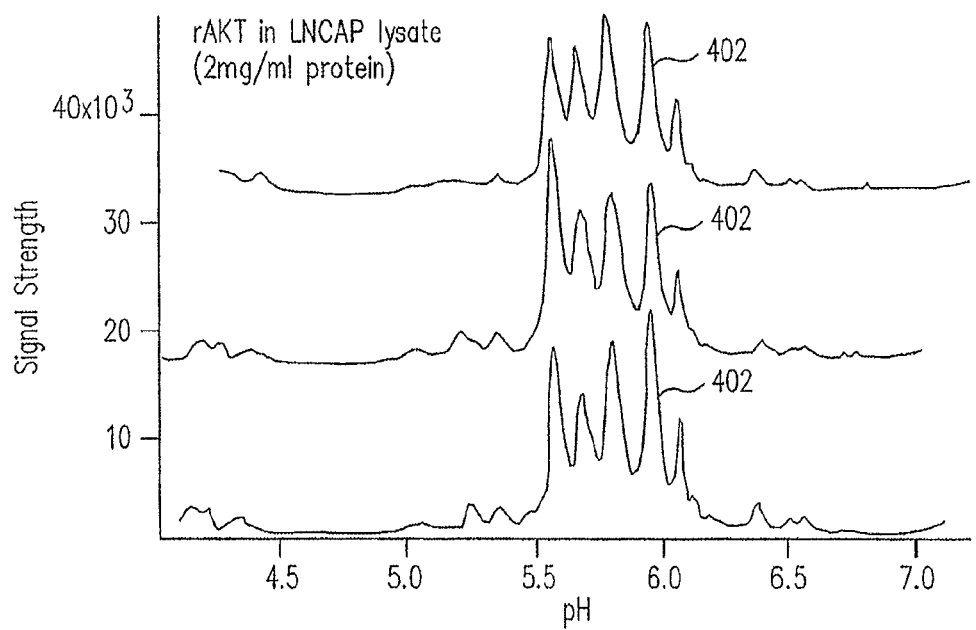
FIG. 20 is a graph of the chemiluminescence data of FIG. 19 aligned by pH.

The following two examples illustrate application of this technique. In a first example of isoelectric separation, recombinant AKT (a human protein) is separated by isoelectric focusing in a 5 to 8 pH gradient. Included in the separation are peptides with known pI values of 5.5 and 6.4. FIG. 19 illustrates the raw data from such an experiment. In this example the raw data is plotted as signal vs. distance, because the entire separation device is imaged to generate the signal from chemiluminescence. Trace 402 is the chemiluminescence signal generated from rAKT. Trace 404 is the fluorescence signal from peptide standards that focus at a known pH. The units of the x-axis are pixel positions from the CCD camera used to capture the photon signals and are directly proportional to distance in the separation device. The peaks appearing in the trace 404 of the peptide standards are then used to generate a known function that is applied to each point of the x (distance) axis in order to transform the x-axis from distance to pH as shown in FIG. 20. Those skilled in the art are familiar with the process of using standards of known mobility to create a simple line graph with position in one coordinate axis and a property (pI, time, length, etc.) in another. The position of unknowns can than be placed on the line graph to determine the desired property of the unknown. Alternatively a table can be made using data extrapolated from the known and the target molecules properties can be looked up on the table. In FIG. 20 the same data 402 is plotted as a function of pH in relation to the standards function, and the location of the AKT peaks on the x (pH) axis immediately indicates the pI of the variant of the AKT protein being studied, which is a biophysically relevant quantity.

Figure 21:
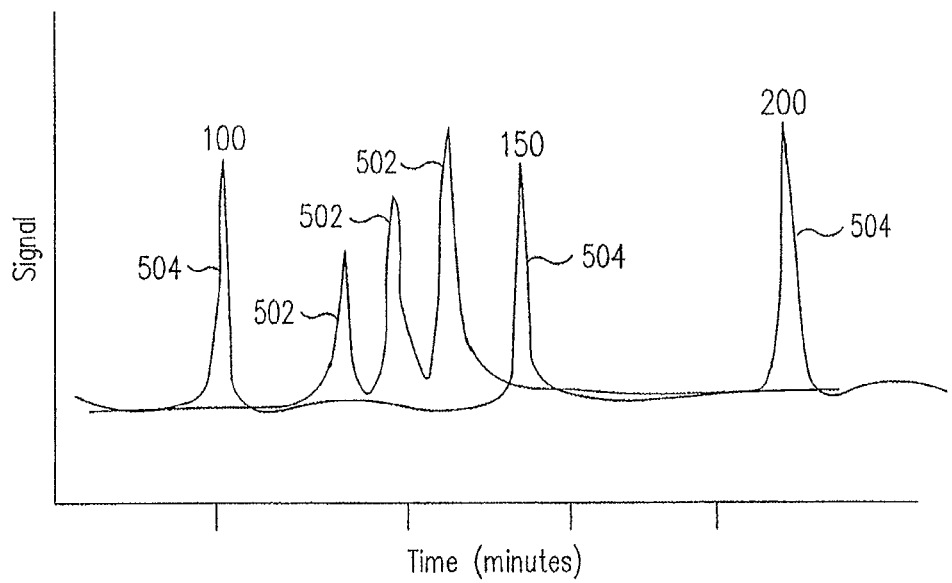
FIG. 21 is a graph of data extracted from a single capillary of nucleotides of known and unknown size.
Figure 22:
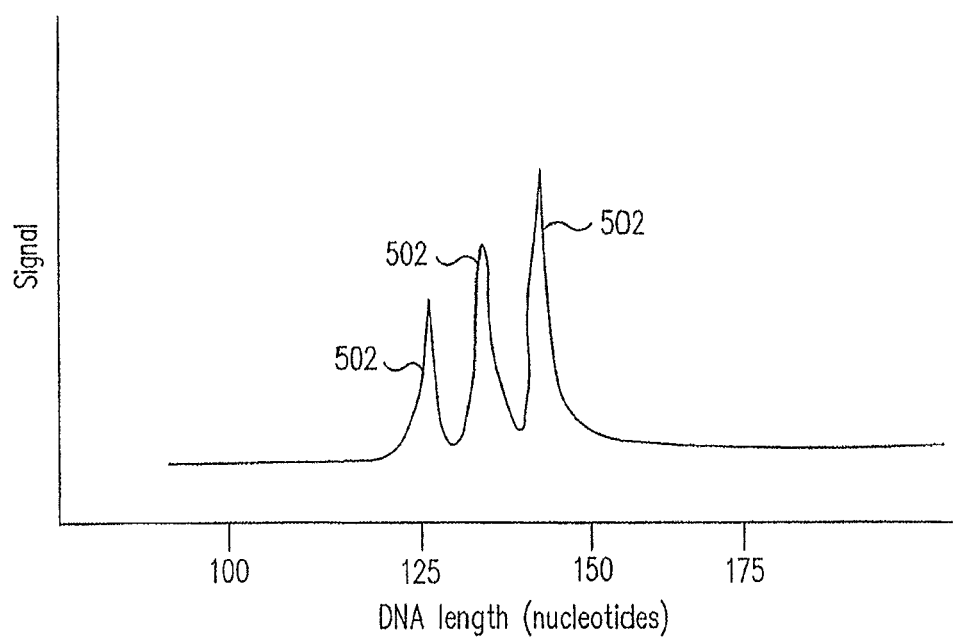
FIG. 22 is a graph of the data of FIG. 21 analyzed to determine the size of the unknowns.

In a second example of DNA sizing, two fragments of DNA are separated on a capillary electrophoresis (CE) instrument. Included in the separation are DNA fragments of a known size. In FIG. 21 the raw data is shown, where the received signal is plotted against time in minutes, because the CE detector generates data at a constant rate throughout the separation. The peaks 502 are generated from DNA fragments with unknown lengths. Peaks 504 are generated by DNA with known lengths as indicated above each peak. The quantitated peaks 504 of the known size DNA fragments are used to generate a function that is applied to each point of the x-axis in order to generate the result data shown in FIG. 22. In this illustration the result data is quantitated in units of signal versus size of the DNA in nucleotides, which is a biophysically relevant quantity.

The following examples are provided for illustration purposes only and are not intended to limit the invention in any way.

ASSAY SYSTEM EXAMPLE 1

Capillaries 60 are presented to the instrument in a format acceptable to the gripper 40. Capillaries may be cleaned, coated, or uncoated. Samples to be analyzed are presented in a standard 96 well microtiter plate 22. Samples are generally cell lysates (or protein samples of various types) mixed with buffers such as ampholytes, pI standards, and photocapture reagents. pI standards are preferably fluorescently labeled. The gripper 40 removes capillaries from a capillary staging rack 30 and brings them in contact with the sample in a microwell. Sample can be drawn up into the capillary by capillary action or vacuum suction. The gripper 40 then places the filled capillary onto a tray 20". The reformatting gripper 40a then rearranges the capillaries on a capillary holder 20. Buffers appropriate for IEF (isoelectric focusing) are placed in the buffer chambers 124 of the capillary holder 20 and the capillary holder is moved into the separation and immobilization module 18. A potential is applied between the buffer chambers 124 and across the capillary inducing isoelectric focusing of the ampholytes, proteins and pI standards. After focusing the potential is turned off and a UV light source is turned on, activating the photo capture chemistry. Alternatively, the light source may be turned on while the potential remains applied. Proteins are thereby immobilized. This immobilization could be to a wall coating of the capillary or indirectly to the capillary (with or without coating) through the formation of a gel. The capillary holder is then moved out of the module 18.

The gripper 40 removes the capillaries from the holder 20 and manipulates them for washing and blocking. At this point buffers are exchanged. Best practice is to use vacuum pressure to exchange solutions, however electrophoresis (EP), electroosmotic (EO) flow, hydrodynamic driven flow, can also be used. The separation buffer is replaced with buffers appropriate for preparing to bring a primary antibody in contact with the protein of interest. Also, denaturing buffers (e.g. those containing detergents, chaotropic agents, etc.) can be used to denature proteins at this step if desired. These may or may not include blocking reagents used in westerns such as milk, casein, or bovine serum albumin. Next, primary antibody is introduced into the capillary. Primary antibody can be flowed in using vacuum pressure or introduced by electrophoresis. Antibodies have a negative charge under native conditions and can be electophoresed. It is possible to have primary antibody labeled with a detection reagent such as a fluorophore or an enzyme suitable for chemiluminescence such as horseradish peroxidase. The primary antibody makes contact and binds to the protein of interest. Excess antibody is washed away either by vacuum pressure, EP, or EO.

Additional washes may be performed to prepare the sample for presentation with a secondary antibody if necessary. Those skilled in the art will be familiar with the use of secondary antibodies used in Western blots. These would be applied in the same manner as specified for the primary antibody.

The gripper 40 then transfers the capillaries 60 to a capillary holder 20 at the detection module 16. This module uses a CCD camera suitable for detection of chemiluminescence. Reagents are presented to one of the buffer reservoirs of the capillary holder. The reagents are introduced into the capillary by hydrodynamic flow. One skilled in the art will recognize that other means of introducing these reagents such as pressure, EP, EO, may be used. The reagents are typical of those used for chemiluminescence such as luminol; other chemiluminescence systems such as alkaline phosphatase can also be used. In another embodiment multiple chemiluminescent and/or fluorescent detection means can be used to detect multiple different analytes in a multiplexed manner. When luminol comes in contact with the labeled sample in the capillary light is produced and is measured by the camera. Long exposures are possible as consumed reagents can be continuously replaced with fresh substrates by flow. In this example a fluorescent excitation source and appropriate lenses and filters are present for detection of fluorescence-labeled pI standards.

Signal is detected along the length of the capillary where the protein of interest lies. This signal is interpreted by software to produce a histogram of signal from one end of the capillary to another. The protein-specific signal can be studied and compared to pI and other standards to determent the properties of interest to the investigator. One skilled in the art will recognize that multiple proteins can be studied in a single capillary.

ASSAY SYSTEM EXAMPLE 2

In this example the process of Example 1 is employed except that the protein of interest is be labeled with a fluorescent molecule. In this example the fluorescent excitation source and optical system detect both the pI standards and the protein of interest. In this example the CCD camera is replaced with a scanning light sensor with a suitable light measuring device such as a photomultiplier tube. Optics capable of detecting multiple types of fluors with different excitation and emission wavelengths are employed.

Variations and extensions of the methods and apparatus described above are fully within the scope of the present invention. The robotic systems of the automated assay system can be segmented and modularized to enable the wash, block and probe functions to be conducted by a dedicated module for these tasks, thereby freeing up the robotics including the grippers to process the next set of capillaries while an experiment is in process. This improves the throughput of the system by allowing preparation for a subsequent experiment to be conducted while the current experiment is ongoing. Modules for these segmented functions can incorporate their own internal mechanisms such as capillary manipulators, pipeting and plate handling, or the system robotics can multitask the functions with a system scheduler. Capillaries can be vertically oriented and dipped into fluid or placed horizontally. Various techniques can be used to move fluids through the capillaries, including electrical, vacuum, pressure, or gravity flow. By retaining capillaries securely in the plates entire plates can be tilted to make fluid contact with an entire row of capillaries or an entire tray in a single operation. Capillaries may be pre-heated to shorten processing times. Multiple pipets may be utilized by the system, allowing pipets to be cleaned during periods when the robotic mechanisms are otherwise idle. Greater numbers of capillaries may be manipulated at one time than the groups of capillaries described above. Any functionality within the system may be duplicated to increase capacity and/or throughput.

What is claimed is:

1. An apparatus, comprising:
    an automated assay system including a baseplate;
    an actuator coupled to the baseplate of the automated assay system and movable with respect to the baseplate in at least one direction;
    a capillary gripper rotatably coupled to the actuator such that the capillary gripper rotates with respect to the actuator from a first position to a second position, the capillary gripper having a plurality of fingers configured to accept and retain a plurality of capillaries, an end of each of the plurality of fingers defining a first plane; and
    a vacuum manifold coupled to the actuator, the vacuum manifold defining a chamber and a plurality of ports pneumatically coupled to the chamber, a portion of the vacuum manifold including the plurality of ports defining a second plane,
    the first plane being in a first orientation with respect to the second plane when the capillary gripper is in the first position, the first plane being in a second orientation with respect to the second plane when the capillary gripper is in the second position, the first orientation being different than the second orientation.

2. The apparatus of claim 1, wherein the capillary gripper includes a plurality of spring clamps, each spring clamp from the plurality of spring clamps is coupled to a finger from the plurality of fingers, each spring clamp from the plurality of spring clamps configured to mechanically retain a capillary from the plurality of capillaries.

3. The apparatus of claim 1, wherein each finger from the plurality of fingers defines an aperture, each aperture being pneumatically coupled to a vacuum source configured to provide a suction to the aperture of a finger from the plurality of fingers such that the suction retains a capillary from the plurality of capillaries.

4. The apparatus of claim 1, wherein the baseplate defines a third plane in a third orientation with respect to the first plane when the capillary gripper is in the first position, the third plane being in a fourth orientation with respect to the first plane when the capillary gripper is in the second position, the third orientation being different than the fourth orientation.

5. The apparatus of claim 1, wherein the vacuum manifold is configured to apply a suction operable to draw fluid into each capillary from the plurality of capillaries when the capillary gripper is in the second position.

6. The apparatus of claim 1, wherein each finger from the plurality of fingers defines a groove, the groove of a finger from the plurality of fingers configured to receive a capillary from the plurality of capillaries such that the groove of the finger partially surrounds the capillary from the plurality of capillaries.

7. The apparatus of claim 1, wherein each finger from the plurality of fingers defines a groove, each groove defines an axis having a third orientation with respect to the first plane in both the first position and the second position.

8. A method, comprising:
gripping a capillary with a capillary gripper in a first position such that the capillary is in a first orientation with respect to a vacuum manifold, the capillary gripper being coupled to the vacuum manifold, the vacuum manifold having a cavity and an aperture;
rotating the capillary gripper with respect to the vacuum manifold from the first position to a second position such that the capillary is in a second orientation with respect to the vacuum manifold and such that an end portion of the capillary is disposed within the aperture and is in pneumatic communication with the cavity;
applying suction to the cavity such that a fluid is drawn into the capillary;
rotating the capillary gripper from the second position to the first position such that the capillary is in the first orientation with respect to the vacuum manifold, the second orientation being different than the first orientation; and
depositing the capillary at a processing station.

9. The method of claim 8, wherein the capillary gripper includes a finger defining a longitudinal axis in a third orientation with respect to a longitudinal axis of the capillary when the capillary gripper is in the first position and the second position.

10. The method of claim 8, wherein the capillary gripper includes a finger defining a longitudinal axis, the longitudinal axis being in a third orientation with respect to the vacuum manifold when the capillary gripper is in the first position, the longitudinal axis being in a fourth orientation with respect to the vacuum manifold when the capillary gripper is in the second position, the third orientation being different than the fourth orientation.

11. An automated assay system, comprising:
a processing station configured to analyze a reagent or sample within a set of capillaries;
at least one microwell plate station;
an actuator;
a gripper rotatably coupled to the actuator such that the gripper rotates with respect to the actuator between a first position and a second position, the gripper operable to simultaneously move a set of capillaries between the processing station and the at least one microwell plate station; and
a vacuum manifold defining a chamber and a plurality of ports, the chamber interconnecting each of the plurality of ports, each port from the plurality of ports configured to receive a tip of a capillary from the set of capillaries when the gripper is in the first position, the tip of the capillary from the set of capillaries being disposed within the chamber when the gripper is in the first position, the tip of the capillary from the one or more capillaries being disposed outside the chamber when the gripper is in the second position.

12. The automated assay system of claim 11, further comprising:
a detection station, the gripper operable to position, using the actuator, the set of capillaries containing the reagent or sample at one of the processing station or the detection station.

13. The automated assay system of claim 11, the automated assay system further comprising: a baseplate, the gripper being rotatable with respect to the baseplate, a portion of the gripper being substantially parallel to the baseplate when the gripper is in the second position, the portion of the gripper being substantially perpendicular to the baseplate when the gripper is in the first position.

* * * * *